United States Patent
Chandraratna

(10) Patent No.: US 6,627,652 B1
(45) Date of Patent: Sep. 30, 2003

(54) METHOD OF TREATMENT WITH COMPOUNDS HAVING SELECTIVE AGONIST-LIKE ACTIVITY ON RXR RETINOID RECEPTORS

(75) Inventor: Roshantha A. S. Chandraratna, Mission Viejo, CA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 08/425,558

(22) Filed: Apr. 20, 1995

Related U.S. Application Data

(63) Continuation of application No. 08/016,404, filed on Feb. 11, 1993, now Pat. No. 5,455,265.

(51) Int. Cl.$^7$ .................. H61K 31/19; H61K 31/34; H61K 31/38

(52) U.S. Cl. .................. 514/448; 514/445; 514/448; 514/438; 514/461; 514/471; 514/473; 514/531; 514/563; 514/569; 514/570; 514/571; 549/60; 549/70; 549/71; 549/72; 549/73; 549/484; 549/479; 549/486; 560/100; 562/490

(58) Field of Search .................. 549/60, 70, 71, 549/72, 73, 484, 479, 486; 560/100; 562/490; 514/445, 448, 438, 461, 471, 473, 531, 563, 569, 570, 771

(56) References Cited

U.S. PATENT DOCUMENTS

| | | | |
|---|---|---|---|
| 4,096,341 A | 6/1978 | Frazer | 560/85 |
| 4,326,055 A | 4/1982 | Loeliger | 568/10 |
| 4,391,731 A | 7/1983 | Boller et al. | 252/299.62 |
| 4,695,649 A | 9/1987 | Magami et al. | 560/86 |
| 4,723,028 A | 2/1988 | Shudo | 562/495 |
| 4,739,098 A | 4/1988 | Chandraratna | 560/8 |
| 4,740,519 A | 4/1988 | Shroot et al. | 548/224 |
| 4,810,804 A | 3/1989 | Chandraratna | 514/311 |
| 4,826,969 A | 5/1989 | Maignan et al. | 536/55.2 |
| 4,826,984 A | 5/1989 | Berlin et al. | 546/134 |
| 4,855,320 A | 8/1989 | Chatterjee et al. | 514/473 |
| 4,895,868 A | 1/1990 | Chandraratna | 514/432 |
| 4,927,947 A | 5/1990 | Chandraratna | 549/484 |
| 4,980,369 A | 12/1990 | Chandraratna | 514/437 |
| 4,992,468 A | 2/1991 | Chandraratna | 514/532 |
| 5,006,550 A | 4/1991 | Chandraratna | 514/456 |
| 5,013,744 A | 5/1991 | Chandraratna | 514/345 |
| 5,015,658 A | 5/1991 | Chandraratna | 514/432 |
| 5,023,341 A | 6/1991 | Chandraratna | 549/23 |
| 5,037,825 A | 8/1991 | Klaus et al. | 514/233.8 |
| 5,045,551 A | 9/1991 | Chandraratna | 514/337 |
| 5,053,523 A | 10/1991 | Chandraratna | 549/398 |
| 5,068,252 A | 11/1991 | Chandraratna | 514/543 |
| 5,089,509 A | 2/1992 | Chandraratna | 514/337 |
| 5,130,335 A | 7/1992 | Chandraratna | 514/510 |
| 5,134,159 A | 7/1992 | Chandraratna | 514/456 |
| 5,162,546 A | 11/1992 | Chandraratna | 549/23 |
| 5,175,185 A | 12/1992 | Chandraratna | 514/445 |
| 5,183,827 A | 2/1993 | Chandraratna | 514/444 |
| 5,202,471 A | 4/1993 | Chandraratna | 562/473 |
| 5,231,113 A | 7/1993 | Chandraratna | 514/510 |
| 5,234,926 A | 8/1993 | Chandraratna | 514/253 |
| 5,248,777 A | 9/1993 | Chandraratna | 546/165 |
| 5,264,456 A | 11/1993 | Chandraratna | 514/461 |
| 5,264,578 A | 11/1993 | Chandraratna | 546/269 |
| 5,272,156 A | 12/1993 | Chandraratna | 514/314 |
| 5,278,318 A | 1/1994 | Chandraratna | 549/23 |
| 5,324,744 A | 6/1994 | Chandraratna | 514/456 |
| 5,324,840 A | * 6/1994 | Chandraratna | 546/318 |
| 5,326,898 A | 7/1994 | Chandraratna | 560/17 |
| 5,344,959 A | * 9/1994 | Chandraratna | 560/100 |
| 5,346,895 A | 9/1994 | Chandraratna | 514/247 |
| 5,346,915 A | 9/1994 | Chandraratna | 514/432 |
| 5,348,972 A | 9/1994 | Chandraratna | 514/432 |
| 5,348,975 A | 9/1994 | Chandraratna | 514/456 |
| 5,349,105 A | 9/1994 | Chandraratna | 564/163 |
| 5,354,752 A | 10/1994 | Chandraratna | 514/252 |
| 5,380,877 A | 1/1995 | Chandraratna | 549/60 |
| 5,391,753 A | 2/1995 | Chandraratna | 546/63 |
| 5,399,561 A | * 3/1995 | Chandraratna | 514/448 |
| 5,399,586 A | 3/1995 | Davies et al. | 514/448 |
| 5,407,937 A | 4/1995 | Chandraratna | 514/256 |
| 5,414,007 A | 5/1995 | Chandraratna | 514/365 |
| 5,426,118 A | 6/1995 | Chandraratna | 514/337 |
| 5,455,265 A | * 10/1995 | Chandraratna | 514/448 |

FOREIGN PATENT DOCUMENTS

| | | | |
|---|---|---|---|
| DE | 3316932 | 11/1983 | C07C/63/66 |
| DE | 3524199 | 1/1986 | C07C/63/66 |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King and William L. Klima, *J. Org. Chem.* 45 No. 12, 1980 p. 2526.

Sporn et. al. in *J. Amer. Acad. Derm.* 15:756–764 (1986).

(List continued on next page.)

*Primary Examiner*—Paul J. Killos
(74) *Attorney, Agent, or Firm*—Gabor L. Szekerea; Robert J. Baran; Martin A. Voet

(57) ABSTRACT

Process of treatment of mammals, including humans to treat diseases or conditions of the type which are normally treated with retinoid-like compounds is disclosed, with pharmaceutical compositions containing an active compound which is a selective agonist of the RXR retinoid receptor sites in preference to the RAR retinoid receptor sites. A compound is defined to be a selective agonist of the RXR receptor site if the compound is at least approximately ten times more effective as an agonist in the RXR receptor sites than in the RAR receptor sites.

27 Claims, 8 Drawing Sheets

FOREIGN PATENT DOCUMENTS

| | | | |
|---|---|---|---|
| DE | 3531722 | 3/1986 | C07C/69/76 |
| DE | 3602473 | 7/1987 | C07C/43/215 |
| DE | 3708060 | 9/1987 | C07D/311/04 |
| DE | 3715955 | 11/1987 | C07C/15/58 |
| EP | 0098591 | 1/1984 | C07D/333/54 |
| EP | 0130795 | 1/1985 | C07D/311/58 |
| EP | 170105 A | 2/1986 | C07C/65/38 |
| EP | 0176032 | 4/1986 | C07C/65/38 |
| EP | 0176033 | 4/1986 | C07D/261/18 |
| EP | 176034 A | 4/1986 | C07C/63/66 |
| EP | 0206751 | 12/1986 | C07D/215/18 |
| EP | 0210929 | 2/1987 | C07C/63/331 |
| EP | 0245825 | 11/1987 | C07D/231/04 |
| EP | 0253302 | 1/1988 | C07D/213/16 |
| EP | 0272921 | 6/1988 | C07D/213/80 |
| EP | 0284288 | 9/1988 | C07D/401/04 |
| EP | 0303915 | 2/1989 | A61K/31/255 |
| EP | 0315071 | 5/1989 | C07C/63/66 |
| EP | 0350846 | 7/1989 | C07D/311/58 |
| GB | 2164938 | 4/1986 | C07C/43/215 |
| GB | 2190378 | 11/1987 | C07C/39/21 |
| WO | 8500806 | 2/1985 | A61K/31/00 |
| WO | 8504652 | 10/1985 | A61K/31/19 |
| WO | WO9116051 | 10/1991 | A61K/31/44 |
| WO | WO9206948 | 4/1992 | C07C/69/86 |
| WO | 9321146 | 10/1993 | C07C/69/76 |

OTHER PUBLICATIONS

A Convenient Synthesis of Ethynylarenes and Diethynylarenes by S. Takahashi, Y. Kuroyama, K. Sonogashira, N. Hagihara, *Synthesis 1980* p. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, p. 334–335, 354.

Synthesis of 2,2'–Diacyl–1,1'–biaryls. Regiocontrolled Protection of . . . by Mervic, et al, *J. Org. Chem.,* No. 45, p. 4720–4725, 1980.

A Dopamine Receptor Model and Its Application in the Design of a New Class of Rigid Pyrrolo[2,3–g]isoquinoline Antipsychotics, Gary L. Olson, et al. *American Chemical Society, 1981,* Vo. 24, No. 9, pp. 1026–1031.

6.2.3 Conformational Restriction, Williams, et al., *Drug Discovery and Development, 1987* The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In vitro, C. C. Zouboulis, *The Journal of Investigative Dermatology,* vol. 96, No. 5, May 1991, pp. 792–797.

Organ maintenance of human sebaceous glands: in vitro effects of 13–cis retinoic acid and testosterone, John Ridden, et al., Journal of Cell *Science,* Vo. 95, 1990,pp. 125–136.

Characterization of Human Sebaceous Cells In Vitro, Thomas I. Doran, et al., *The Journal of Investigative Dermatology,* vol. 96, No. 3, Mar., 1991.

Synthesis and Evaluation of Stilbene and Dihydrostilbene Derivatives as Potential Anticancer Agents That Inhibit Tubulin Polymerization by Cushman, Mark et.al. *J.Med. Chem 1991,* 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters,* vol. 1, No. 4, pp. 211–214, 1991.

Ney et al., Chemical Abastracts, vol. 108(1987) 68312g.

Di–and Tri–methoxystyryl Derivatives of Heterocyclic Nitrogen Compounds by Bahner, C.T. et al. Arzneim–Forsch,/Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry, 1989, 32,* pp. 1098–1108.

Hofmann, Sandra L., M.D. Am. J. Med. Sci., vol. 304, No. 3, 1992, p. 202–231.

Aneskievich, et al., Mol. Cell. Biol., vol. 12, No. 11 1992 p. 4862–4871.

* cited by examiner

Compound 1 (AGN 191701)

Compound 1 (AGN 191701)

Compound 1 (AGN 191701)

Compound 1 (AGN 191701)

Compound 1 (AGN 191701)

Compound 3 (AGN 191985)

Compound 5 (AGN 191758)

Compound 1 (AGN 191701)

METHOD OF TREATMENT WITH COMPOUNDS HAVING SELECTIVE AGONIST-LIKE ACTIVITY ON RXR RETINOID RECEPTORS

CROSS-REFERENCE TO RELATED APPLICATION

The present application is a continuation of application Ser. No. 08/016,404, filed on Feb. 11, 1993, to be issued as U.S. Pat. No. 5,455,265.

FIELD OF THE INVENTION

The present invention is directed to methods of administering to mammals including humans, compounds which are selective agonists of the retinoid receptor sites designated as RXR, and which lack substantial teratogenic activity and have substantially reduced skin toxicity. The present invention is also directed to pharmaceutical compositions adapted for administering said compounds to mammals, including humans.

BRIEF DESCRIPTION OF THE PRIOR ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The compounds developed in the prior art with retinoid like properties, are, however, not without disadvantages. Several such prior art compounds cause serious irritation when applied to the skin (which is an important mode of application for treatment of skin conditions) and cause mucotaneous toxicity when administered orally as well. Many of the prior art compounds having retinoid like activity are teratogenic. Teratogenecity or teratogenic activity can be defined as an undesirable effect of a drug on a developing fetus. It is generally accepted in the art that pregnant females, and even females who are not pregnant but in the child-bearing age should avoid teratogenic drugs.

In light of the foregoing, there is a significant need in the prior art for pharmaceutical compositions, methods of treatment and new chemical entitities which are effective for treatment of the diseases and conditions for which retinoid like compounds are usually applied, and which have reduced or no teratogenic activity and cause no significant irritation on the skin.

With respect to specific compounds or classes of compounds having retinoid like or other biological activity, the following examples are noted.

German Patent DE 3316-932 A describes 1-phenyl-2-chromanyl-propylene derivatives and sulphur and nitrogen analogs. Specific examples of this disclosure are ethyl p-[(E)-2-(4,4-dimethyl-6-chromanyl, thiochromanyl or 1,2,3,4-tetrahydro-6-quinolinyl)propenyl]-1-benzoate.

U.S. Pat. No. 4,826,984 describes benzopyranyl (chromanyl) and benzofuranyl-propenyl benzoic acids and esters thereof, an example being ethyl-p-(2-(4,4-dimethyl chroman-6-yl)-propenyl benzoate.

European EP 130 795 A discloses 4,4-dimethyl-6-chromanyl alkenyl benzoic acid derivatives, thiochromanyl and tetrahydroquinolinyl analogs. The 2 and 7 positions of the chroman, thiochroman and tetrahydroquinoline ring moieties in these compounds are not substituted.

The publication WO 8500-806 A discloses 4,4. -dimethyl-chroman-6-yl and 4,4-dimethyl-thiochroman-6-yl-ethenyl and 4,4-dimethyl-chroman-6-yl and 4,4-dimethyl-thiochroman-6-yl-propenyl benzoic acid, its esters and the corresponding thiophencarboxylic acid and other heterocyclic acid analogs. The 2 position of the chroman or thiochroman ring is unsubstituted.

The publication EP 350 846 A discloses p-(2-(3,4-dihydro-4,4-dimethyl-dihydrochroman-7-yl)-propeneyl) benzoic acid ethyl ester and related compounds.

The publication WO 8504 652 A discloses certain diaryl substituted propenyl compounds, an example being ethyl (E)-4-[2-(4-isopropylphenyl)-propenylbenzoate.

European patent EP 206 751 A discloses 2-substituted phenyl-alkenyl-quinoline derivatives as inhibitors of leukotriene synthesis. An examples of a compound of this reference are (E)-4-(3-(2-(quinolin-2-yl)-1-methylethenylphenoxy)butyric acid.

Published European patent application 0 098 591 A1 describes rodenticidal disubstituted propenyl compounds, an example of which is ethyl p-[2-(4,5,6,7-tetrahydro-4,4,7,7-tetramethylbenzo[b]thien-2-yl)propenyl benzoate, and another example is ethyl 6-[(E)-2-(4,5,6,7-tetrahydro-4,4,7,7-tetramethylbenzo[b]thien-2-yl)propenyl] nicotinate.

Great Britain Patent GB 2190-378 describes tetramethyl-tetrahydronaphthylpropenylphenol compounds, examples of which are ortho, meta or para (E)-2-(5,6i7,8-tetrahydro-5,5,8,8-tetramethyl-2-naphthyl)propenyl)phenol.

German Patent DE 3602-473 A discloses aralkenylphenol derivatives, examples of which are (E)-1-(4-hydroxyphenyl)-2-(5,6,7,8-tetrahydro-5,5,8,8-tetramethyl-2-naphthyl)propene and (E)-1(4-methoxyphenyl)-2-(5,6,7,8-tetrahydro-5,5,8,8-tetramethyl-2-naphthyl)propene.

European patent EP 176 033 A discloses isoxazolylvinyl indane and tetrahydronaphthalene derivatives, an example of which is (E)-5-[2-(3-fluoro-5,5,8,8-tetramethyl-5,6,7,8-tetrahydro-2-naphthyl)-1-propenyl]-isoxazole-3-carboxylic acid.

The publication EP 303 915 discloses indanyl and tetrahydronaphthyl and substituted phenyl propenes as retinoids, where the phenyl substituent is sulfur substitited. An example of the disclosed compounds is methyl 4-(2-(5,6,7,8-tetrahydro-5,5,8,8-tetramethyl-2-naphthyl(propenyl) phenylsulphone.

European patent EP 176 032 A discloses 6-styryltetrahydro-naphthalene derivatives, examples of which are (E)-4-[2-(5,6,7,8-tetrahydro-5,5,8,8-tetramethyl-7-hydroxy-2-naphthalenyl)-1-propenyl]benzylalcohol, and E-4-[2-(5,8-dihydro-5,5,8,8-tetramethyl-2-naphthalenyl)-1-propenyl]benzoic acid.

European Patent EP 315 071 discloses 1-benzocycloheptenyl-2-carboxy-phenyl ethylene derivatives, an example of which is ethyl p-(E)-2-(6,7,8,9-tetrahydro-7,7-dimethyl-5H-benzocycloheptene-2-yl) propenyl benzoate.

German Patent DE 3524-199-A discloses stilbene-4-carboxylic acid derivatives, examples of which are [E-2-(3,4-diisopropylphenyl)propenyl]benzoic acid, [E-2-(3-tert-butylphenyl)propenyl]benzoic acid.

European Patent EP 245 825 describes heterocyclylalkenyl benzene derivatives, examples of which are 3-(β-(4'-hydroxy-3'-methoxyphenyl)ethenyl)-5-methyl-pyrazole and 5-(β-(4'-hydroxy-3',5'-bis-(1,1-dimethylethyl)phenyl)-ethenyl)-5-methylpyrazole.

European Patent EP 210 929 A discloses certain 2-aryl-naphthalene derivatives useful in dermatological and ophthalmologycal medicaments. Intermediates leading to the synthesis of these compounds include certain arylethenyl benzene derivatives.

German Patent DE 3531 722 A discloses certain benzonorbornene derivatives which have vitamin A like activity.

Great Britain patent GB 2164-938 A discloses certain 2-styryl-naphthalene derivatives having retinoid like activity. An example of the compounds is 2-(4-methyl-β-methyl-styryl)naphthalene.

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,723,028 discloses 1,2-diphenylethene (stilbene) derivatives which have retinoid like activity.

U.S. Pat. No. 4,740,519 discloses certain aromatic heterocycle derivatives which have retinoid like activity.

Published European Patent Application 0130795 discloses ethene derivatives, where the ethene moiety is substituted by a substituted phenyl group and by a substituted chroman, thiochroman or quinoline group. The compounds are useful for inhibiting the degradation of cartilage in mammals.

Several co-pending applications and recently issued patents of the present inventor, which are assigned to the assignee of the present application, are directed to further compounds having retinoid like activity and/or to methods of treatment of mammals including humans with retinoid-like compounds.

Relatively recently it was recognized in the prior art that there is more than one retinoid cellular response pathway in biological systems, and that at least two main families of receptors exist in biological systems for naturally occurring retinoid hormones. These relatively recent developments in the prior art are described in the articles: D. J. Mangelsdorf et al. "Nuclear receptor that identifies a novel retinoic acid response pathway", Nature Vol 345 May 17, 1990 pp 224–229; and J. N. Rottman et al. A Retinoic Acid-responsive Element in the Apiloprotein AI Gene Distinguishes between Two Different Retinoic Acid Response Pathways, Molecular and Cellular Biology, July 1991, pp 3814–3820. The following additional references relate to retinoic acid receptors. M. Petkovich et al. "A human retinoic acid receptor which belongs to the family of nuclear receptor", Nature, Vol. 330, Dec. 3, 1987, pp 444–450; V. Giguere et al. "identification of a receptor for the morphogen retinoic acid", Nature, Vol 330, Dec. 17, 1987, pp 624–629; N. Brand et al. "Identification of a second human retinoic acid receptor", Nature, Vol 332, Apr. 28, 1988, pp 850–853; A. Krast et al., "A third human retinoic acid receptor, hRAR", Proc. Nat'l. Acad. Sci. USA, Vol 86, July 1989, pp 5310–5314; D. J. Mangelsdorf et al., "Characterization of three RXR genes that mediate the action of 9-cis-retinoic acid", Genes & Development, Vol. 6, 1992, pp. 329–344.

The two main families of retinoid receptors are termed RAR (Retinoic Acid Receptor) and RXR (Retinoid X Receptor) in the art, and each of these two families is known to have subtypes, which are designated by letters of the Greek alphabet, such as $RAR_\alpha$, $RAR_\beta$ and $RAR_\gamma$. The above-noted article by D. J. Mangelsdorf et al. states that some retinoid-like compounds (retinoic acid analogues) activated the RAR receptors much more strongly than the RXR receptors.

SUMMARY OF THE INVENTION

It has been discovered in accordance with the present invention that retinoid-like compounds which act selectively, and preferably even specifically as agonists of the RXR receptor sites in preference over the RAR receptor sites, possess desirable therapeutic properties associated with retinoids but without having one or more undesirable side effects of retinoids, such as teratogenecity or skin toxicity. For the purposes of the present invention, a compound is defined to be a specific or at least selective agonist of the RXR receptor site if the compound is at least approximately ten times more potent as an agonist at the RXR receptor sites than at the RAR receptor sites.

Accordingly, the present invention relates to methods of treating animals of the mammalian species, including humans, and particularly females of child-bearing age and pregnant females, with a non-teratogenic pharmaceutical composition comprising one or more specific or selective RXR agonist retinoid-like compounds as the active ingredient, for treatment of the diseases or conditions against which retinoid like compounds are useful, namely as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The present invention is also directed to the pharmaceutical compositions used in the above-noted methods of treatment.

The present invention particularly covers methods for treating diseases and conditions where retinoid like compounds are effective for treatment, but their use is limited because of their generally known teratogenecity or skin toxicity.

BRIEF DESCRIPTION OF THE DRAWING FIGURES

DETAILED DESCRIPTION OF THE INVENTION

Figure 1:
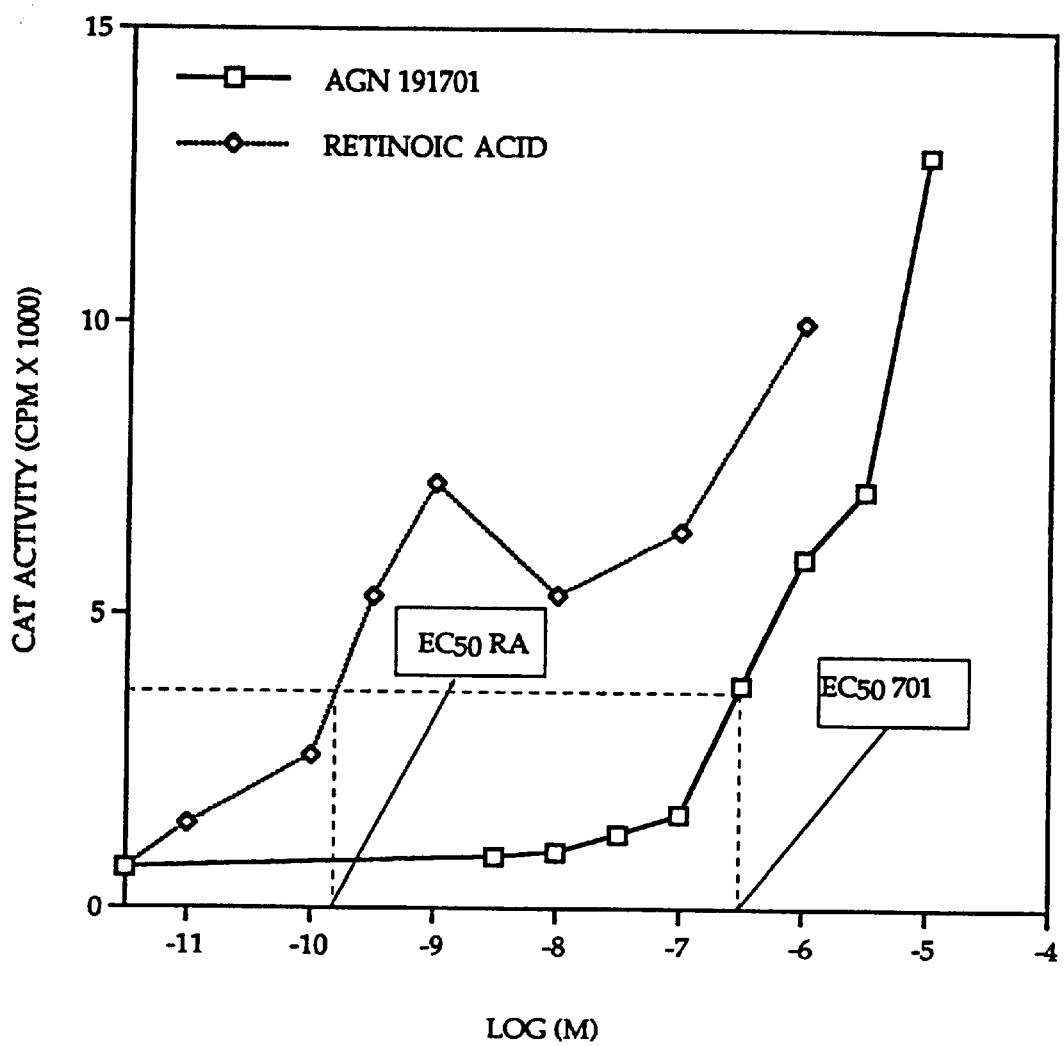
FIG. 1 is a graph showing data and the alculation of $EC_{50}$, obtained in the Cationic Liposome Mediated Transfection Assay on the $RAR_\alpha$ receptor, with a test compound (AGN 191701, Compound 1), and with the reference compound trans retinoic acid.
Figure 1:
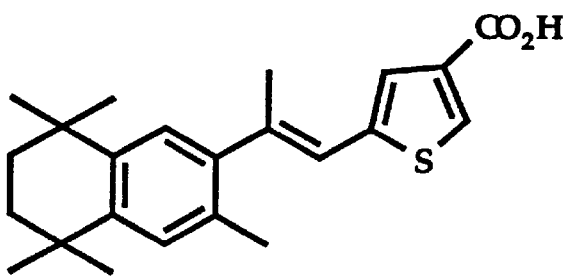

Compounds which are used in the pharmaceutical compositions and methods of treatment of the present invention are selective or specific agonists of the RXR receptor sites, in preference over the RAR receptor sites. In accordance with the present invention, a compound is considered a selective RXR agonist if that compound is at least 10 times more effective as an agonist of the RXR receptors than of the RAR receptors. Preferably, the compounds utilized in accordance with the present invention are specific agonists of the RXR receptor. Specificity in this regard is defined in the sense that a specific RXR agonist does not act as an agonist of the RAR receptor to any measurable or biologically significant extent. An assay by which the activity of a test compound as a potential agonist of the RXR and RAR receptor sites is determined, is performed substantially as reported by Feigner P. L. and Holm M. (1989) Focus, 11 2 and is described below first in principle and thereafter in the form of specific instructions how to perform the assay.

In connection with this assay it is known that retinoic acid receptors are a member of the steroid/thyroid receptor super family and that they contain domains which are interchangeable within individual receptors. Thus, plasmids for chimeric retinoid receptors containing estrogen DNA binding domain and estrogen response element chloramphenicol acetyl-transferase enzyme are constructed and are grown in specific cultured bacteria. These plasmids respectively code for chimeric $RAR_\alpha$, $RAR_\beta$, $RAR_\gamma$, $RXR_\alpha$ receptor proteins, and for the chloramphenicol acetyl A transferase (CAT) enzyme protein. The bacteria with these plasmids are obtainable in accordance with the procedure set forth in the article titled "Nuclaer Retinoic Acid Receptors: Cloning, Analysis, and Function", M. Pfahl et al., Methods in Enzymology 189, p256–270 (1990) which is incorporated herein by reference. The detailed procedure how to isolate the DNA plasmids from the respective bacteria is also set forth below in detail, in the form of specific instructions under the title "Super-coiled Plasmid Isolation".

Thus, in accordance with the test procedure, DNA plasmid which codes for one of the chimeric $RAR_\alpha$, $RAR_\beta$, RAR, or $RXR_\alpha$ receptor proteins is transfected into cultures of HeLa cells. It is for this purpose that HeLa cells are grown in a medium during the first day of the assay detailed below as the "Cationic Liposome Mediated Transfection Assay". In the transfection procedure, which is performed during the second day of the transfection assay, the DNA plasmid coding for the CAT enzyme is also added to each cell culture, in addition to the respective chimeric $RAR_\alpha$, or $RAR_\beta$ etc. coding plasmid. As is known and will be readily understood by those skilled in the art, especially in view of the above-cited M. Pfahl et al. article, chimeric retinoid receptors involved in this assay include a ligand binding domain which recognizes and binds specific agonist molecules, such as retinoic acid and analogs. These chimeric protein receptors (which were constructed in accordance with the teachings of the M. Pfahl et al. article) also contain a a DNA binding domain, which is capable of binding to the "estrogen response element" (a DNA fragment) attached to the DNA plasmid coding for the CAT enzyme. The nature of the interaction is such, that only if an agonist (such as retinoic acid or analog) is bound to the ligand binding domain of the respective $RAR_\alpha$, $RAR_\beta$. etc. receptor, only then is the receptor bound through its DNA-binding domain to the estrogen response element of the estrogen-response-element-chloramphenicol-acetyl transferase-construct (ERE-CAT). In other words, through multiple interactions CAT enzyme is manufactured by the HeLa cell in this assay only if an appropriate agonist ligand binds to the ligand binding site of the respective retinoid receptor.

The estrogen response-element-chloramphenicol acetyl-transferase construct (ERE-CAT) is itself obtained in accordance with the procedure described in the article Ryssel G. U. et al. Cell, Volume 46, pp 1053–1061 (1986), which is incorporated herein by reference. This procedure per se is well known in the art. The specific detailed procedure how to isolate and obtain the estrogen-response-element chloramphenicol-acetyl-transferase-construct (ERE-CAT) from bacteria is descibed in the procedure titled "Super-coiled Plasmid Isolation".

In addition to the foregoing, lipofectin (LF) is also added to each cell culture. The purpose of the lipofectin is to facilitate transport of plasmids through the cell membrane. The lipofectin used in the procedure is available commercially.

As it will be well understod by those skilled in the art, as a result of transfection with the respective DNA plasmid coding for $RAR_\alpha$, or $RAR_\beta$ etc. chimeric receptors and as a result of transfection with the ERA-CAT (which codes for the CAT enzyme as described above), the aforementioned plasmids are incorporated into the HeLa cells cultured in the assay. The retinoid receptor plasmids undergo transcription (into m-RNA) and subsequent translation into the corresponding chimeric receptor protein. Therefore, the Hela cells cultures obtained in this manner manufacture the respective $RAR_\alpha$, $RAR_\beta$, $RAR_\gamma$, or $RXR_\alpha$ chimeric receptor protein. As a result of transfection with the ERA-CAT the cell cultures of this asssay also contain the genetic information for manufacturing the CAT enzyme. However, as is noted above, the latter genetic information is not transcribed, and the CAT enzyme is not manufactured by the respective cell cultures of this assay, unless an appropriate agonist compound binds to and activates the respective $RAR_\alpha$, $RAR_\beta$, $RAR_\gamma$, or $RXR_\alpha$ chimeric receptor protein in the cell and this activated agonist-receptor complex binds to the estrogen response element of the ERE-CAT construct.

The assay procedure is continued by adding, on the third day of the assay, an appropriate reference compound and the test compound (agonist or prospective agonist) to the respective HeLa cell culture, preferably in varying concentrations. As a result of this addition, if the test compound is an agonist, it binds to the respective $RAR_\alpha$, $RAR_\beta$, $RAR_\gamma$, or $RXR_\alpha$ chimeric receptor protein, and consequently the genetic information which codes for the CAT enzyme is transcribed in the cell, whereby CAT enzyme is made by the cell.

After lysis of the cell, which is performed on the fourth day of the below-detailed assay procedure, the activity of CAT enzyme in aliquot portions of the lysate is measured. This is done by incubating the lysate with chloramphenicol and tritium labeled acetyl coenzyme A. As a final measurement, the amount of tritium labelled acetyl chloramphenicol, which is formed in the enzymatic reaction involving the CAT enzyme, is measured in a scintillation counter.

The reference compound is retinoic acid (all trans) for the assays involving the $RAR_\alpha$, $RAR_\beta$, and $RAR_\gamma$ receptors, and 4-(E)-2-(5,6,7,8-tetrahydro-3,5,5,8,8-pentamethylnaphthalen-2-yl)-propen-1-yl]benzoic acid (AGN 191440, also designated Compound 6 in this application) for the $RXR_\alpha$ chimeric receptor. The data obtained in the assay are evaluated and expressed as follows. For each test compound and for each subspecies of the RAR receptors a graph (or the mathematical equivalent of a graph) is prepared where the "counts per minute" (cpm) obtained in the scintillation counter measurements are plotted (on the y axis) against the concentration of the test compound. A similar graph (or mathematical equivalent) is prepared for retinoic acid. $EC_{50}$ of the test compound is defined as that concentration of the test compound which provides ½ (50 %) of the maximum cpm number (maximum CAT enzyme activity) obtained in the same receptor in the same assay with the reference compound retinoic acid. This is illustrated in the graph of FIG. 1.

Figure 2:
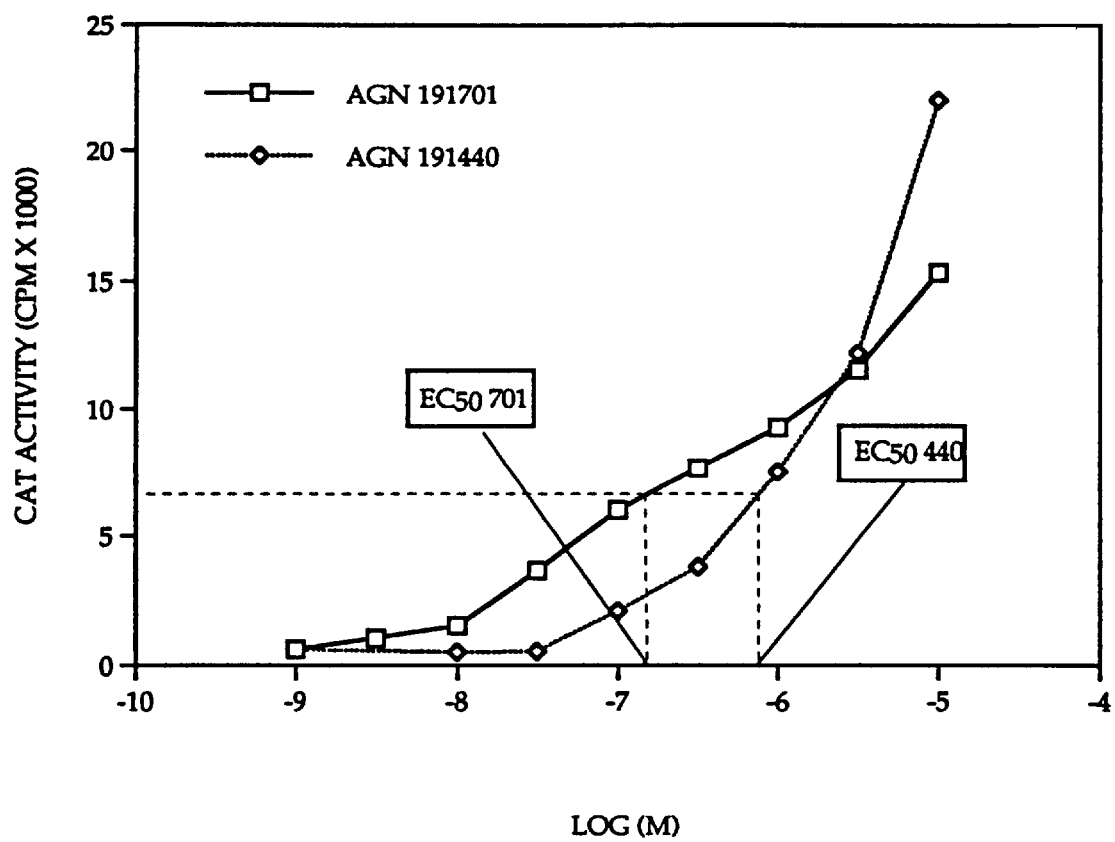
FIG. 2 is a graph showing data and the calculation of $EC_{50}$, obtained in the Cationic Liposome Mediated Transfection Assay on the $RXR_\alpha$ receptor, with a test compound (AGN 191701, Compound 1), and with the reference compound AGN 191440 (Compound 6).
Figure 2:
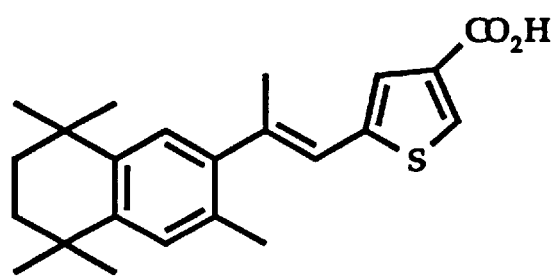

To evaluate and express the data obtained in the assay for the $RXR_\alpha$ receptor, the same type of graph (or mathematical equivalent) is prepared for the test compound, and also for the reference compound AGN 191440, Compound 6. This reference compound is a known agonist of the $RXR_\alpha$ receptor site. $EC_{50}$ is that concentration of the test compound which gives one half (50%) of the counts per minute (CAT enzyme activity) of the maximum cpm obtained with AGN 191440 on the same receptor in the same assay. A graph illustrating the foregoing is shown in FIG. 2.

SUPERCOILED PLASMID ISOLATION

Large Scale 1L Prep

DNA Isolation

1. Place cells on ice for 15 minutes. Harvest the bacterial cells (*E. coli*) by spinning down in 250 ml nalgene tubes at 7 k rpm, 10 minutes at 4° C. using JA14 rotor, Beckman J2-21 M centrifuge. Discard the supernatant.

2. To each cell pellet add 1.0 ml Solution I, vortex to resuspend the pellet. Transfer the 1.0 ml of cells from one bottle to another. Transfer this to a 50 ml Oakridge tube. Use 4 ml of Solution I and wash the bottles again transferring from one bottle to the next. Transfer this also into the Oakridge tube. Using a pipet bring up the total volume to 16 ml with Solution I and mix the solution. Transfer 8 ml to a second Oakridge tube. Store at room temperature for 5 minutes.

Solution I 50 mM glucose, 25 mM Tris-Cl pH8, 10 mM EDTA pH8

3. Add to each tube 18 ml of freshly prepared Solution II. Mix contents gently by inverting the tube several times. Store on ice for 10 minutes. After this time the liquid should be clear with no aggregates. (If there are clumps, then the cells were not resuspended well enough previously.)

Solution II

1% sodium dodecylsulfate (SDS), 0.2N NaOH (4 ml 10% SDS, 0.8 ml 10N NaOH, 35.2 ml water)

4. Add 12 ml, (or as much as will fit) of ice-cold Solution III. Mix the contents of tube by inverting it sharply several times. A white flocculent precipitate should appear. Store on ice for 10 minutes.

Solution III

Prepare as follows: to 60 ml 5M potassium acetate, add 11.5 ml of glacial acetic acid and 28.5 ml water.

5. Centrifuge at 4° C. in a Beckman J2-21M centrifuge, JA20 rotor, 17 k rpm for 30 minutes.

6. Pipet approximately 12 ml of supernatant from the Oakridge tubes into 6 baked Corex tubes. Add 0.6 volumes of isopropanol (7.2 ml) mix by inversion and store at room temperature for 15 minutes to precipitate DNA.

7. Warm Beckman centrifuge by spinning JA20 rotor at 14 k rpm for 15 minutes at 20° C.

8. Pellet DNA at 20° C. in the J2-21M centrifuge, JA20 rotor at 10.5 k rpm for 30 minutes (use adapters for corex tubes).

9. Pour off supernatant, dry inside of tube with pasteur pipet on a vacuum flask.

10. Dry in vacuum dessicator for 10 minutes (Longer drying time will make it hard to dissolve pellet).

Purification of Plasmid DNA by Centrifugation to Equilibrium in CsCl Density Gradients 11. Dissolve pellet by adding 1 ml TE (10 mM Tris-Cl pH 8, 1 mM EDTA pH8) to each corex tube. Place tubes in 37° C. water bath to help pellets to dissolve faster (15–30 minutes).

12. Transfer liquid from like batch into one tube. Bring volume to 8.5 ml with TE.

13. Add 100 µl RNase, DNase free (2U/µl, source Boehringer Mannheim Biochemical (BMB)).

14. Add 400 µl of 10 mg/ml Ethidium Bromide.

15. Add 9.0 g CsCl and mix using a pasteur pipet.

16. Add solution to two 13×51 mm Beckman polyallomer quick-seal centrifuge tubes.

17. Spin at 50 k rpm for 12 hours in Beckman ultracentrifuge, VTi65.2 rotor, 20° C.

18. After ultracentrifugation, two bands of DNA should be visible. The upper band consists of linear bacterial DNA and nicked circular plasmid DNA. The lower band consists of closed circular plasmid DNA. Only the lower CsCl-banded DNA is removed from the tube with a 3-ml syringe fitted to an 21-gauge needle (Needle is inserted into the side of the tube and 1.5–2 ml is removed).

19. Preparation for Second CsCl centrifugation:
(9 ml—vol 1st CsCl band)—number g CsCl
(9 ml—vol 1st band—100 µl 10 mg/ml Ethidium Bromide—50 µl RNase)—ml TE pH 8.0
Combine 1st band, TE, CsCl, RNase and EtBr.
20. Add solution to 2 quick-seal tubes.
21. Spin at 50 k for 12 hours or 60 k rpm for 4 hours in ultracentrifuge, VTi65.2 rotor, 20° C.
22. Remove twice CsCl-banded DNA (lower band only) to a 5 ml Falcon snap tube (as in step 18).

Extraction of Ethidium Bromide

23. Under fumehood add an equal volume isoamyl alcohol, vortex, spin at room temperature at 1500 rpm in Beckman TJ-6 centrifuge for 3 minutes.
24. Transfer bottom aqueous layer to fresh tube. Repeat 3–4 times or until aqueous layer is clear (no pink color).
25. Transfer clear aqueous layer to Spectra/Por 3 dialysis tubing, mwco 3500. (Tie a knot in the bottom of tubing before clamping dialysis tubing.) Add liquid using a pasteur pipet. Clamp top or dialysis tubing. Using a rubber band suspend tubing in 2.8 L TE (28 ml 1M Tris-Cl, pH8, 5.6 ml 0.500M EDTA, pH8). Always handle dialysis tubing carefully, with gloves.
26. Dialyze aqueous phase against several changes of 2.8 L TE pH8 (1× 2–4 hours, overnight and 1× 2–4 hours the next day).
27. In the tissue culture hood transfer the dialyzed DNA into sterile microcentrifuge tubes. Label tubes and store at −20° C.

CATIONIC LIPOSOME-MEDIATED TRANSFECTION

Reference: Felgner, P. L., and Holm, M. (1989) Focus 11, 2.

USE STERILE TECHNIQUE THROUGHOUT

Grow up HeLa or CV-1 cells in T-125 culture flask. Cells are passed twice a week usually on Monday and Friday (0.5 ml cells into 15 ml medium)

DAY 1: Plating Cells

1. Trypsinize and collect cells from T-162 $cm^2$ culture flask. Count cells using a hemocytometer. Usually, this amount of cells is enough for sixteen 12-well plates.
2. Based on the cell number, dilute cells in medium (D-MEM low glucose, 10% fetal bovine serum (FBS), 2 mM Glu) to a concentration of 60,000 cells per well.
   Example cell calculation:
   want 40,000 cells/well and 200 wells
   have (X) cells/ml
   therefore, 40,000 cells/well×200 wells–total # ml cells
   (X) cells/ml
   needed
   Using a Nalge 250 ml Filter Unit Receiver add total #ml cells to medium and bring final volume to 200 ml. Mix well by pipetting.
3. Add 1.0 ml of cells per well using a sterile 12.5 ml combitip (setting 4). Shake plates back and forth (do not swirl). Incubate at 37° C. in a humidified 5% $CO_2$ environment overnight. Cells are about 40% confluent prior to transfection.

Transfection: DAY 2 PREPARATION DNA/LIPOFECTIN COMPLEX

1. Using 50 ml polystyrene tubes prepare Lipofectin (LF) and DNA separately. Determine vol of LF and DNA needed for 2 µg LF/well, 500 ng ERE-CAT DNA/well, 100 ng ER/RAR DNA per well. Determine total volume needed for experiment. (DNA concentration will vary between each plasmid prep and the following calculations will need to be adjusted accordingly.)

| DNA (prep date) | µl/well | #wells | vol DNA | Vol Opti-Mem |
|---|---|---|---|---|
| α | | | | |
| β | | | | |
| τ | | | | |
| X | | | | |
| CAT | | | | |
| LF lot # | µl/well | #wells | µl LF | Vol Opti-Mem |

Separately dilute LF and DNA in Opti-Mem media to a volume of 25 ul×#wells: Vol Opti-Mem 1=(25 ul×#wells)–total vol. DNA or LF.

2. Add the diluted LF to the diluted DNA and swirl tube gently. Let sit room temperature for 10 min.
3. Aspirate off the medium from the wells and wash 2× using 0.5 ml Opti-Mem I (sterile 12.5 ml combitip, setting 2).
4. Add the DNA/LF complex to vol of Opti-Mem: (450 µl×# wells). Invert tube to mix. Using a sterile 12.5 ml combitip (setting 2) add 500 µl to each well. Shake plates back and forth to mix, do not swirl.
5. Incubate the cells for 6 hours at 37° C. in a humidified 5% $CO_2$ incubator.
6. After 6 hours add 0.5 ml medium to each well (D-MEM low glucose, 20% FBS charcoal treated, 2 mM Glu) Use 12.5 combitip setting 2 and place back in the incubator.

DAY 3: Drug Addition 1. 18 hours after the start of transfection add retinoids in triplicate (10 µl) using a sterile 0.5 ml combitip (setting 1) and incubate for 20–24 hours at 37° C. in a humidified 5% $CO_2$ environment.

DRUG DILUTIONS $$\frac{weight\ (g)}{ACETONE} \times \frac{1}{mol.\ wt\ (g/mol)} \times \frac{100\ ml}{.005\ mol/L} = \frac{ml}{L}$$

Example: Retinoids are dissolved in acetone to a conc. of 5 mM and further diluted to 1 mM in EtOH. If retinoids do not go into solution place tube in hot water for 5 seconds followed by vigorous vortexing. Each experiment may have a different dilution scheme. For 2 concentrations per order of magnitude use a 3.16-fold dilution as follows: To labeled sterile 12×75 mm tubes (Falcon 2063) add 1080 ul of 100% EtOH. Using the 1 mM solution transfer 500 ul to the next tube (316 µM). Vortex and repeat the transfer to the next tube down the line. Some retinoids are light sensitive, especially RA and 13-cis RA, and should be used with a red or very dim light. Log in the amount of compound used.

Example

| Drug Dilution | Vol add to well | Final: -log [conc.] |
|---|---|---|
| 5 mM (initial) | | |
| 1 mM | 10 | 5.0 |
| 316 µM | 10 | 5.5 |
| 100 µM | 10 | 6.0 |

-continued

| Drug Dilution | Vol add to well | Final: -log [conc.] |
|---|---|---|
| 31.6 μM | 10 | 6.5 |
| 10 μM | 10 | 7.0 |
| 3.16 μM | 10 | 7.5 |
| 1 μM | 10 | 8.0 |
| 316 nM | 10 | 8.5 |
| 100 nM | 10 | 9.0 |
| 31.6 nM | 10 | 9.5 |
| 10 nM | 10 | 10.0 |
| 3.16 nM | 10 | 10.5 |
| 1.0 nM | 10 | 11.0 |

Day 4 MIXED PHASE CAT ASSAY
1. Wash cells in 12 mm wells once with 0.50 ml 1×PBS (no Ca/Mg).
2. Using a 5 ml combipipet (setting 1) add 100 μl of a ice cold 1% Triton, 1 mM Tris-Cl pH7.8, 2mM EDTA pH8, DNase I. Prepared as follows:
LYSIS BUFFER (Hypotonic Buffer)
  2.0 mg DNase I (Sigma)
  4.925 ml water
  50.0 μl 100% Triton X-100 (BMB Lot #
  5.0 μl 1M Tris-Cl pH 7.8
  20.0 μl 0.5M EDTA pH 8
  5.0 ml
3. Place on ice for 60 minutes. Agitate occasionally.
4. Transfer 50 μl lysate from 3 wells at a time using titertrek multichannel pipet with tips attached to channels #1, #3, #6 to 96 U-bottom well (Costar). Place (unused lysate) plates at −20° C.
5. Using a 1.25 ml combipipet (setting 1) add 50 μl premix per well, gently shake plates and incubate 37° C. for 2 hours.

| Vol. per Blank | Vol per reaction × __ (#assays) = total vol. |
|---|---|
| 47.0 | 27.0 μl buffer I (250 mM Tris-Cl pH 7.8, 5 mM EDTA (Date: |
| 1.5 | 1.5 μl 1 mM HCl |
| *** | 20.0 μl 5 mM Chloramphenicol (make fresh in buffer I) Lot# |
| 0.75 | 0.75 μl 4 mM Acetyl CoA in water (make fresh) Sigma Lot# |
| 0.80 | 0.80 μl 3H-Acetyl CoA (New England Nuclear) #NET-290L, 200 mCi/mmol) |

6. Using a titertrek multichannel pipet add 100 μl of 7M Urea into each reaction well to quench the reaction. Do six at a time (Urea-Mallincrokt AR).
7. Using a titertrek multichannel pipet transfer 200 μl reaction mixture into a 5 ml plastic scintillation vial (Research Products International #125514). Do three reactions at a time (Urea-Mallincrokt AR).
8. Add 1 ml 0.8% PPO/Toluene (3.2 g PPO/4 L Toluene) Vortex vigorously for 5 seconds and allow the phases to separate for 15 minutes. Count cpm for 2.0 min-Beckman LS 3801 (Toluene-Mallinckrodt ScintillAR). (PPO=2,5 Diphenyloxazole-RPI Lot #A3071.

Table 1 illustrates the comparative RAR and RXR agonist activity of certain examplary compounds in accordance with the invention. The activity of the compounds on the RAR receptor sites is indicated separately for the respective $RAR_\alpha$, $RAR_\beta$ and $RAR_\gamma$ receptor sites. The structure of each compound indicated in Table 1 is provided in the description below. Compound 7 (AGN 191183) is not within the scope of the invention, receptor data for this compound are provided for comparison.

TABLE 1

| | $EC_{50}$ | | | |
|---|---|---|---|---|
| Compound # | $RAR_\alpha$ | $RAR_\beta$ | $RAR_\gamma$ | $RXR_\alpha$ |
| 1 | NA | 3349 | 1073 | 67 |
| 2 | NA | NA | NA | 1063 |
| 3 | NA | NA | NA | 1309 |
| 4 | >10,000 | >10,000 | >10,000 | 516 |
| 5 | — | — | — | 139 |
| 7 (AGN 191183) | 19 | 1.0 | 0.3 | >10,000 |

In addition to the activity as selective or specific agonists of the RXR receptor site, the general retinoid-like activity of the RXR selective or specific compounds which are used in the pharmaceutical compositions and methods of treatment of the present invention can also confirmed by the following assay procedures, generally known in the art as indicators of retinoid-like activity.

An assay involving human sebocyte cultures measures the inhibition of $^3$H-thymidine into cells, and thus measures inhibition of DNA synthesis and thus an anti-proliferative effect on sebocyte (i.e. a sebostatic effect). This assay is also considered a specific assay for effectiveness of a compound as a potential anti-acne drug. The test is conducted as follows.
SOURCE OF SKINS:
Face-lift or forehead reduction skins from cosmetic surgeries were used as sources of human sebaceous gland cells (sebocytes).
ISOLATION OF SEBOCYTES:
Isolated sebocytes were plated in type 1 collagen coated-dishes in DMEM/F12 (1:1) medium supplemented with 8% fetal bovine serum, 2% human serum, 10 ng/ml epidermal growth factor, 1 nM cholera toxin, 1 μM hydrocortisone, and penicillin/streptomycin/amphotericin B. Secondary cultures were prepared by plating Dispase dissociated cells in collagen coated 24-well plates.
PROLIFERATION STUDIES ($^3$H-THYMIDINE INCORPORATION):
Sub-confluent secondary cultures were treated with the test compounds or ethanol vehicle every 2–3 days for 8 days in the above medium from which the total serum concentration was reduced to 2% and hydrocortisone was not included. During the last 6 hours of treatment, the cultures were labeled with 2 μCi/ml $^3$H-thymidine. DNA from the cells were extracted by thichoroacetic acid and perchloric acid, and assayed for radioactivity by scintillation counting and for content of DNA by the diphenylamine colorimetric method. The results were expressed as CPM/μg DNA, or as per cent of vehicle control which incorporated about 1,000–1,500 cpm/μg DNA.

Figure 3:
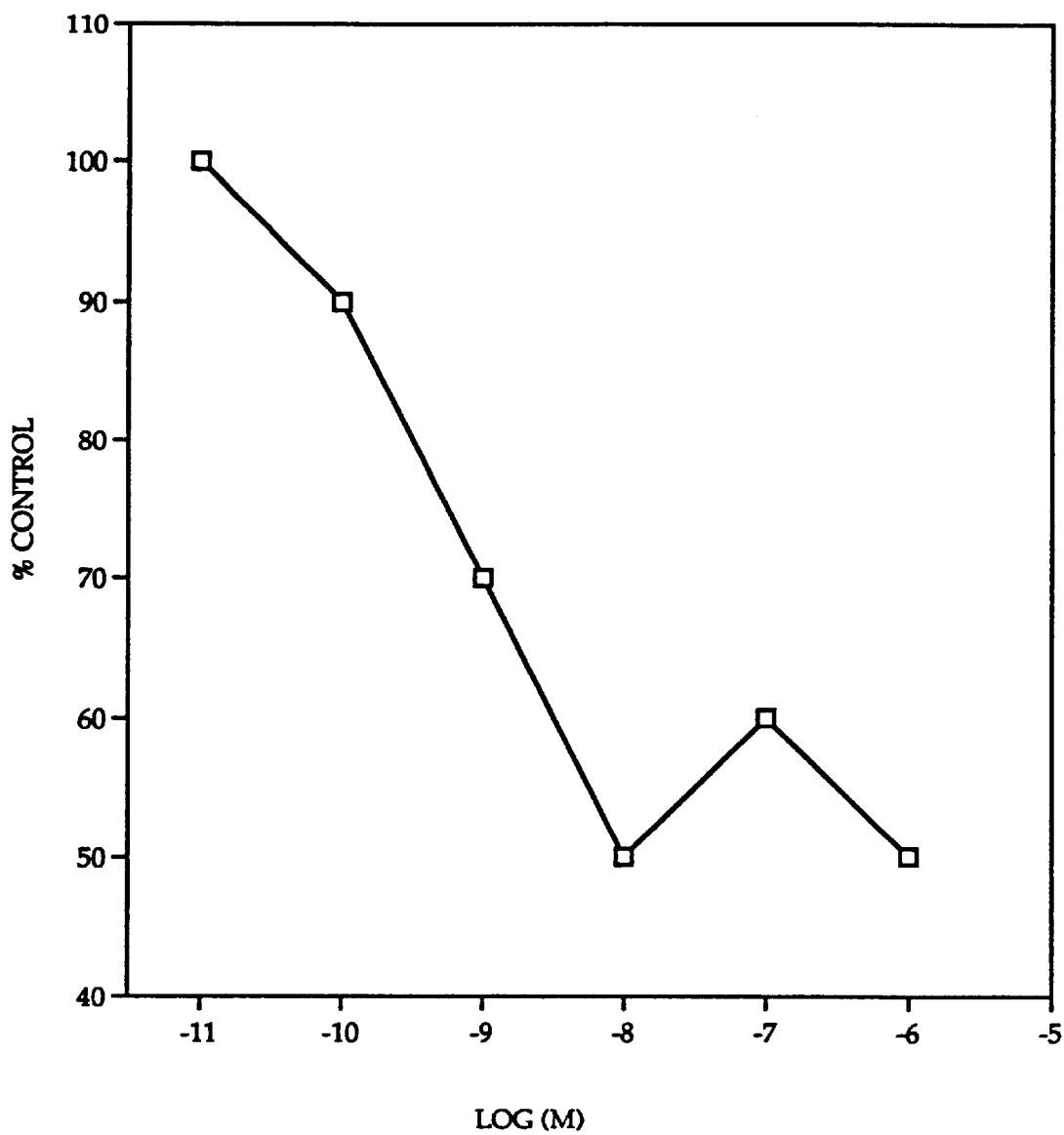
FIG. 3 is a graph, showing as percentage of control, the incorporation of $^3H$-thymidine (a measure of DNA synthesis) as a function of concentration of AGN 191701 (Compound 1) in the $^3H$-thymidine incorporation assay in sebocytes.
Figure 3:
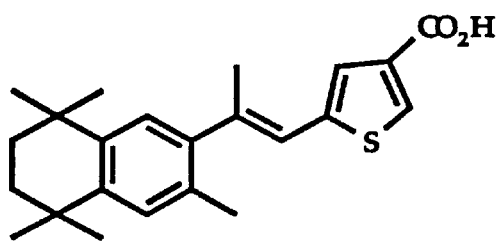

As the graph of FIG. 3 shows, depicting the results of this test for a compound which is within the scope of the present invention, designated as AGN 191701 (also designated as Compound 1 in this patent application), this compound is an effective retinoid.

Another assay in which the retinoid like activity of the compounds used in accordance with the invention can be confirmed are the HL-60 transglutaminase induction and HL-60 differentiation assay, the procedures of which are described as follows.
DIFFERENTIATION:_HL-60 CELLS NITROBLUE TETRAZOLIUM REDUCTION ASSAY (NBT REDUCTION ASSAY)

HL-60 cells were grown as a suspension culture in T-162 CM² flasks in serum-free RPMI 1640 medium supplemented with insulin (5 μg/ml), transferrin (5 μg/ml), and selenium (3 nM). The cells (1×10⁵/well in 24-well dishes) were treated with serial dilutions of test compounds in the above RPMI 1640 medium which was additionally supplemented with 0.2 mM dibutyryl cyclic adenosine monophosphate, a component found to be necessary for efficient differentiation of the cells. Ethanol was used in the vehicle control cultures. After 3 days of incubation at 37° C. in a 5% $CO_2$ incubator, nitroblue tetrazolium (NBT) and tetradecanoylphorbol acetate (TAP), at final concentrations of 0.1% and 100 ng/ml, respectively, were mixed with the cells and incubated at room temperature for 15 to 30 minutes. Differentiated HL-60 cells acquired a purple deposit of formazan (NBT positive cells) from the reduction of NBT. The cells were then fixed in 10% paraformaldehyde and pelleted by centrifugation. The cell pellets were resuspended in a small volume of phosphate buffer saline. The number of NBT positive cells and the total number of cells of each cell suspension was determined by counting in a hemacytometer. The mean of quadruplicate cultures was expressed as per cent of NBT positive cells.

Figure 4:
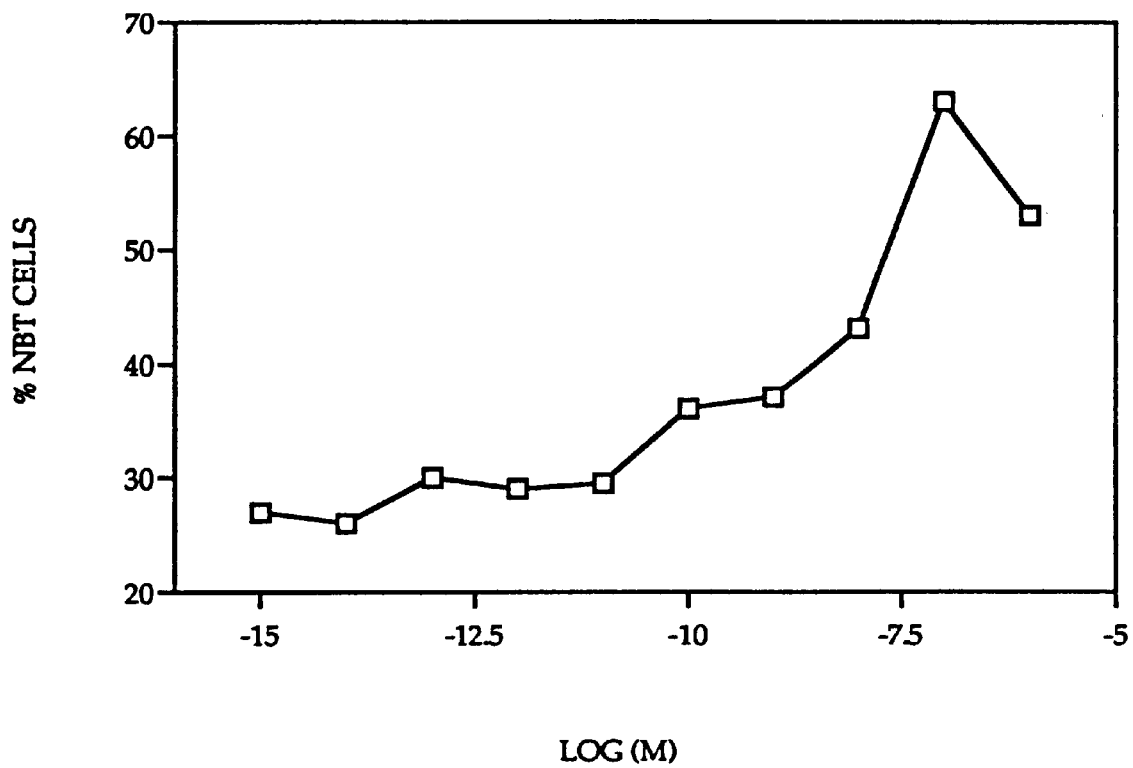
FIG. 4 is a graph showing the results of the HL 60 cell NBT Reduction (cell differentiation) assay with compound AGN 191701 (Compound 1).
Figure 4:
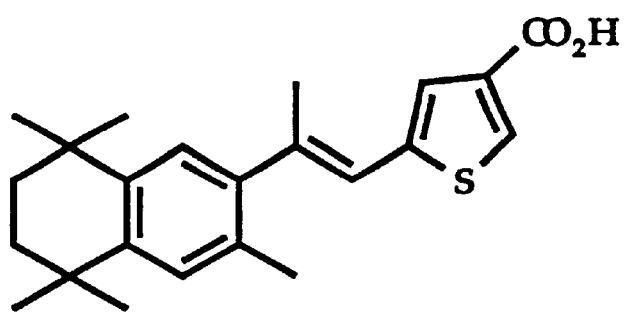

As it will be readily understood by those skilled in the art, differentiation of cells in this assay is a marker of useful retinoid like activity. The results of this assay for the compound AGN 191701 (Compound 1), is shown in the graph of FIGS. 4.

TISSUE TRANSGLUTAMINASE ASSAY (tTGASE) IN HL-60 CELLS

HL-60 cells were grown as a suspension culture in T-162 cm² flasks in serum-free RPMI 1640 medium supplemented with insulin (5 μg/ml), transferrin (5 μg/ml), and selenium (3 nM). The cells (1×10⁶ cells/well, in 6-well dishes) were treated with serial dilutions of test compounds in the above RPMI 1640 medium which was additionally supplemented with 1 nM dibutyryl cyclic adenosine monophosphate, a component found to be necessary for efficient differentiation of the cells. Ethanol was used in the vehicle control cultures. After 1 days of incubation at 37° C. in a 7.5% $CO_2$ incubator, the cells were collected in a set of tubes and pelleted by centrifugation. The cells were lyzed in a buffer containing 20 mM Tris-HCl, pH 7.5, 1 mM EDTA, and 0.5% Triton X-100. An aliquot of the cell lysate was assayed for tTGASE activity in a reaction mixture containing 20 mM Tris-HCl, pH 7.5, 5 mM $CaCl_2$, 2 mg/ml dimethylcasein, 15 mM B-mercaptoethanol and 50 μCi/ml [2,3-³H] putrescine dihydrochloride. The reaction was carried out for 60 minutes in a 37° C. shaking water bath. The reaction was stopped by an addition of 10% trichloroacetic acid containing 0.1% putrescein. An aliquot of the stopped reaction mixture was spotted on Whatman 3 MM filter discs. The filter discs, along with the control blank filter discs, were washed twice with 5% trichloroacetic acid containing 0.1% putrescein and twice with methanol. After drying under a heat lamp, the radioactivity in the filter discs was determined by scintillation counting. An aliquot of the cell lysates was also assayed for protection concentration by the Bradford method (Bio-Rad). After subtracting the radioactivity from the control blank filter discs, the data were calculated and expressed as pmol/min/mg protein.

Figure 5:
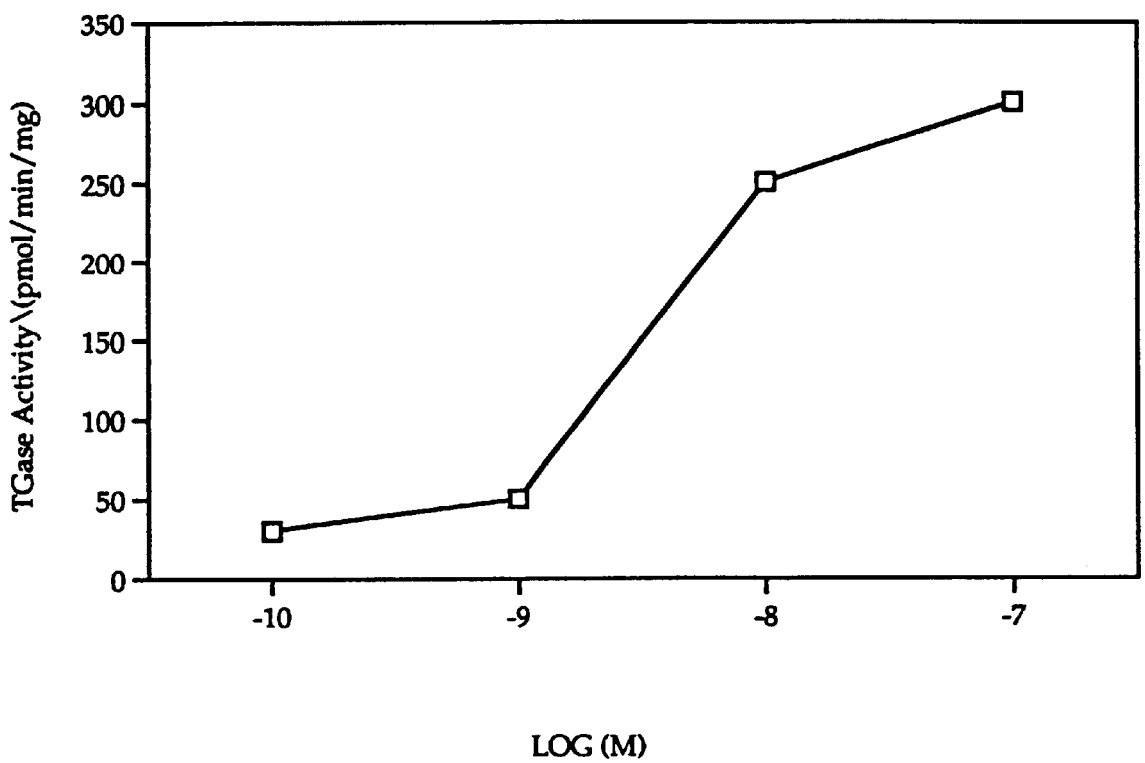
FIG. 5 is graph showing the results of the HL 60 Cell transglutaminase assay for AGN 191701 (Compound 1).
Figure 5:
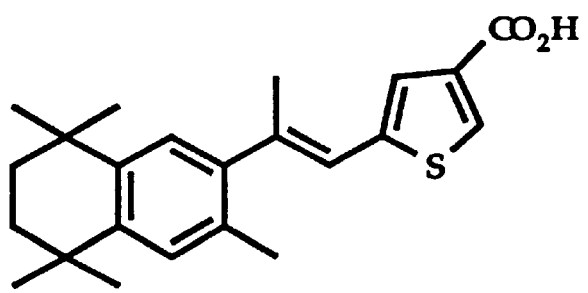
Figure 6:
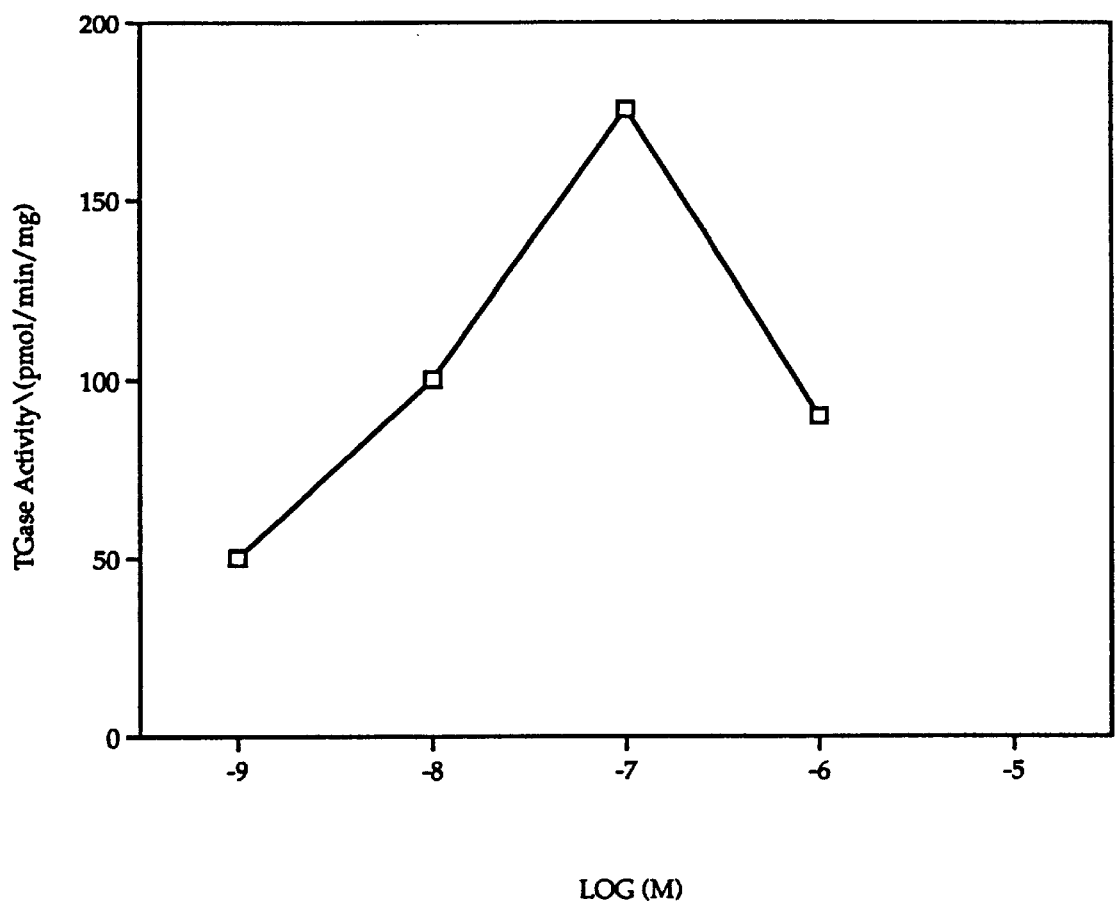
FIG. 6 is a graph showing the results of the HL 60 Cell transglutaminase assay for AGN 191985 (Compound 3).
Figure 6:
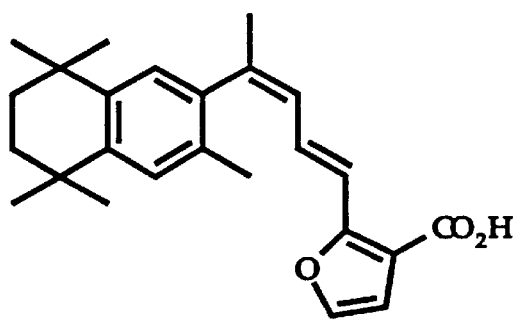
Figure 7:
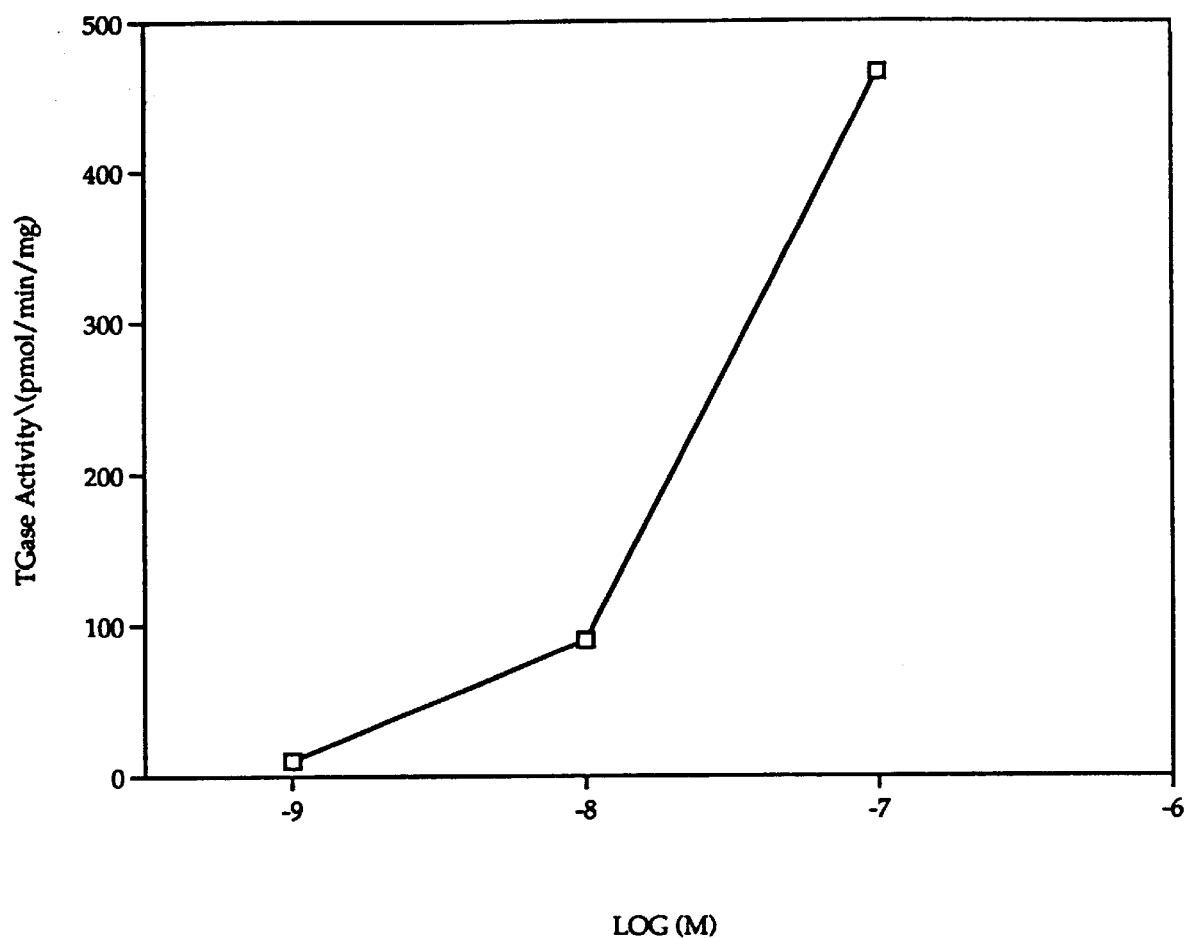
FIG. 7 is a graph showing the results of the HL 60 Cell transglutaminase assay for AGN 191758 (Compound 5).
Figure 7:
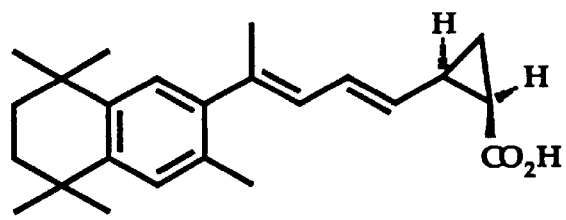

As is well understood in the art, induction of tranglutaminase activity in the just-described assay is an early marker of retinoid like activity. The graphs of FIGS. 5, 6 and 7 respectively show the results of this test for compound AGN 191701 (Compound 1), AGN 191985 (Compound 3) and for AGN 191758 (Compound 5) which are in the scope of the present invention.

The specific or selective RXR agonist compounds used in the pharmaceutical compositions and methods of treatment of the present invention have no teratogenic activity, or are substantially less teratogenic than comparable prior art compounds. The lack of teratogenecity of these compounds is demonstrated by an in vivo teratology study involving gestating ICR mice. The methodology of the study is described as follows:

Animals

ICR mice (Ace Animals, Boyertown, Pa.) were used. Mature male and virgin female ICR mice were housed in environmentally controlled rooms and acclimatized to a 12 hour light/dark cycle (light cycle 6 A.M. to 6 P.M.) for 2 weeks prior to use. All animals were maintained on Purina Lab Chow and tap water ad libitum. A group of 3–4 females was caged with a single male of proven fertility for 4 hours. Presence of a vaginal plug immediately afterward was regarded as evidence of successful mating, and this day was designated as day 0 of gestation.

Teratology

A single oral dose (0.1, 1.0, 10 or 100 mg/kg) of the test drug was administered on the morning (10 A.M.) of day 11 of gestation. All animals were killed by cervical dislocation under mild ether anesthesia on day 17 of gestation. Upon laparotomy, the fetuses were examined for external malformations and weighed; one-half of each litter was then fixed in 95% ethanol and processed for staining of the skeleton by the rapid, alizarin red-S dye method. These preparations were examined under a dissection microscope to screen for abnormalities in the axial and the appendicular skeleton. The other half of each litter was fixed in Bouin's solution and examined by freehand razor serial sectioning to screen for anomalies of the brain, face, and palate.

Differences in dose-related incidence of malformations and resorptions were assessed by computing percentages of affected conceptuses among total implantation sites. The groups were compared statistically by a method based on Student's t-tests of arcs in square root transformed percentages. Values at 0.05 probability level were considered significant. The median effective dose was calculated by logarithmic curve fitting of the dose-response data.

TABLE 2

| Compound | Dose (mg/kg) | # Litters Treated | # Litters Normal | % Resorbed | Teratogenic Effects | |
|---|---|---|---|---|---|---|
| | | | | | % Cleft Palate | % Limb Defects |
| AGN 191701 (Compound 1) | 1 | 1 | 1 | 18 | 0 | 0 |
| | 10 | 3 | 3 | 14 | 0 | 0 |
| | 100 | 3 | 2 | 2 | 19 | 22 |
| AGN 191183 (Compound 7) | 0.01 | 5 | 2 | 3 | 29 | 20 |
| | 0.1 | 4 | 0 | 30 | 100 | 100 |
| | 1 | 2 | 0 | 100 | — | — |
| | 10 | 2 | 0 | 100 | — | — |

Results of the above-noted teratogenecity study are indicated in Table 2. As it can be seen from Table 2, AGN 191701 (also designated in this application as Compound 1) is practically not teratogenic. The teratogenecity data of the RXT selective Compound 1 should be contrasted with the data for the RAR selective Compound 7. It is apparent that Compound 7 is much more teratogenic than Compound 1.

An in vitro bioassay which measures inhibition of chondrogenesis (bone formation) in chick embryo cells is considered a classic measure of teratogenecity. The assay is conducted as follows:

High-density "spot" cultures of limb bud mesenchymal cells were used to compare the ability of various concentrations of test drugs to suppress chondrogenic differentiation as a bioassay. Forelimb buds of mouse embryos on day 12 of gestation (54±2 somites) were dissociated in a trypsin-EDTA solution, and the resultant single-cell suspension was plated as 20-$\mu$l spots (200,000 cells/spot) on plastic culture dishes. Retinoid concentrations ranging from 0.3 ng/ml to 3 $\mu$g/ml (1 nM–10 $\mu$M) were added to the culture medium (Eagle's MEM+10% fetal bovine serum, GIBCO) 24 hours after initial plating. Control cultures received only the vehicle (ethanol, concentration$\leq$1% by vol); Retinoic acid was used as a positive control in another set of cultures.

The cultures were terminated 96 hours after plating, at which time the medium was removed and the cells were fixed for 1 hour in 10% formalin containing 0.5% cetylpyridinium chloride. The cultures were rinsed in acetic acid and stained for 1 hour in 0.5% Alcian blue solution at pH 1.0, differentiated in 3% acetic acid, and then dehydrated in ethanol and scored for chondrogenesis under the microscope. An absence or reduction in the number of cartilage nodules in stained cultures as compared with control cultures was taken as a measure of suppression of chondrogenesis. The number of cartilage nodules stained in the whole spot, mean number of nodules, and standard deviations were calculated for four replicate cultures per treatment. The median concentration causing a 50% inhibition of chondrogenesis compared with controls ($IC_{50}$) was calculated by logarithmic curve fitting of the dose-response data.

As it can be seen in the accompanying Table 3, the compound AGN 191701 (Compound 1) which is RXR selective in accordance with the present invention has an $IC_{50}$ of 19.0 $\mu$/ml in this assay. In contrast, the RAR selective compound AGN 191183 (Compound 7) has an $IC_{50}$ of 0.003. Thus, Compound 1 is approximately $6.3 \times 10^4$ times less teratogenic in this assay than Compound 7.

TABLE 3

| Compound | $IC_{50}$ ($\mu$g/ml) |
|---|---|
| AGN 191701 (Compound 1) | 19.0 |
| AGN 191183 (Compound 7) | 0.003 |

Figure 8:
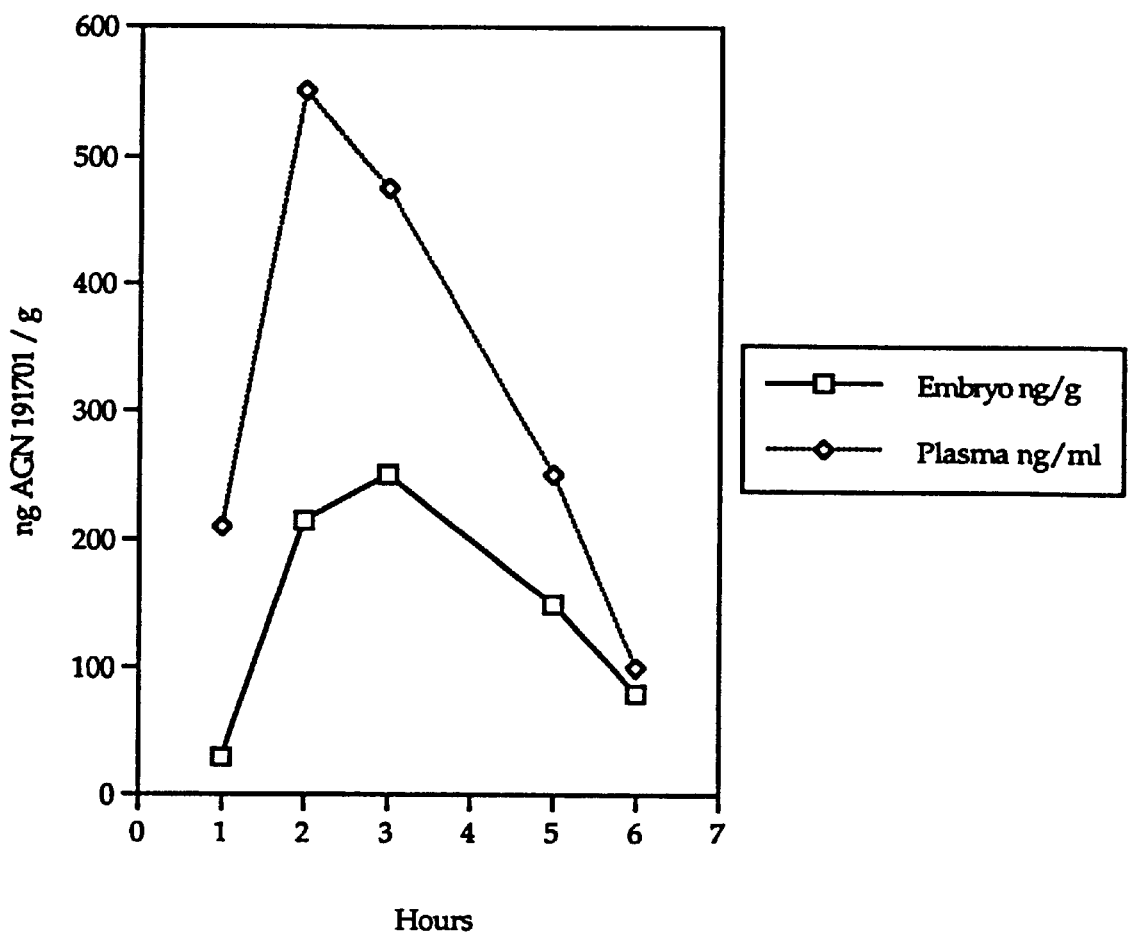
FIG. 8 is a graph showing the concentration of compound AGN 191701 (Compound 1) in nanograms per ml, or nanograms per gram as indicated on the chart, in the plasma and embryo of mice at various times after oral intubation of a single dose of 10 mg/kg of the compound.
Figure 8:
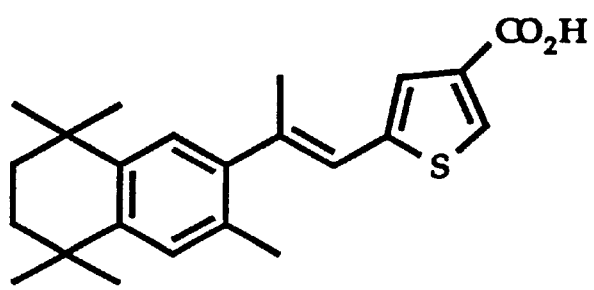

In connection with the foregoing data it should be kept in mind that a pharmacokinetic study involving the oral intubation of mice with a 10 mg/kg dose of compound AGN 191701 (Compound 1) in accordance with the present invention, and subsequent measurement of the concentration of the drug in the maternal plasma and in the embryo, as shown in FIG. 8, revealed that compound AGN 191701 (Compound 1) is in fact present in substantial concentration in the maternal plasma and in the embryo. Yet, as the data of Table 2 show this compound has very little teratogenic effect.

The compounds used in the method of treatment of this invention may be administered systemically or topically, depending on such considerations as the condition to be treated, need for site-specific treatment, quantity of drug to be administered, and similar considerations.

In the treatment of dermatoses particularly, topical administration may be used, though in certain cases such as treatment of severe cystic acne, oral administration may be preferred. Any common topical formulation such as a solution, suspension, gel, ointment, or salve and the like may be used. Preparation of such topical formulations are well described in the art of pharmaceutical formulations as exemplified, for example, by *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoid like compounds will be effected by administration of the therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

Because the RXR specific or RXR selective agonist compounds lack substantial teratogenic effects, treatments of diseases or conditions with such compounds in accordance with the present invention is advantageous, particularly when the treatment is directed to a pregnant female mammal, including human, or to a female mammal, including human, in the child bearing age.

General Embodiments

Definitions

In the chemical description of the compounds provided here as examples of specific or selective agonists of the RXR receptor site (hereinafter RXR agonists), unless specifically defined herein in a manner differing from general usage, all chemical terms have the meaning normally attributed to them by those skilled in organic chemistry. Thus, the term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Preferred esters of the exemplary carboxylic acids within the scope of the present invention are formed with saturated aliphatic alcohols of ten or fewer carbon atoms or the cyclic or saturated aliphatic cyclic alcohols of 5 to 10 carbon atoms, and particularly preferred esters are formed with aliphatic alcohols having 1–10 carbons. Where the ester is derived from compounds within the scope of the present invention which are primary alcohols (B in Formulas 1–5 is —$CH_2OH$) this term covers compounds of the formula —$CH_2OOCR_{11}$ where $R_{11}$ is any substituted or unsubstituted aliphatic, aromatic or aliphatic-aromatic group, preferably with 1–6 carbons in the aliphatic portions. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formulas —$CH(OR_{12})_2$, —$CHOR_{13}O$, —$CR_7(OR_{12})_2$, and —$CR_7OR_{13}O$, where $R_7$ is an alkyl, cycloalkyl or alkenyl group containing 1 to 5 carbons, $R_{12}$ is lower alkyl, and $R_{13}$ is divalent alkyl radical of 2–5 carbons.

A pharmaceutically acceptable salt may be prepared for any compound used in the method of treatment of this invention, if the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The exemplary compounds utilized in accordance with the method of treatment of the present invention, contain at least one double bond, and/or alicyclic ring (such as a cyclopropane ring) and therefore may have trans and cis (E and Z) isomers. In addition, some of the compounds used in the method of treatment of the present invention may contain one or more chiral centers and therefore exist in enantiomeric and diastereomeric forms. Unless, it is specifically indicated otherwise by chemical nomenclature or structure, the scope of the present invention is intended to cover all such isomers per se, as well as mixtures of cis and trans isomers, mixtures of diastereomers and racemic mixtures of enantiomers (optical isomers) as well. In the structural formulas bonds shown with hashed lines indicate a bond below the plane of the paper; bonds shown as a solid triangle indicate a bond above the plane of the paper; trans (E) configuration of substituents about a double bond is indicated by bonds pointing in opposite directions about a double bond, whereas cis (Z) configuration of substituents about a double bond is indicated by bonds pointing in the same direction about a double bond.

The general structures of exemplary specific RXR agonist or selective RXR agonist compounds which are used in the the phramaceutical compositions and methods of treatment of the present invention are provided by general Formulas 1–5 below.

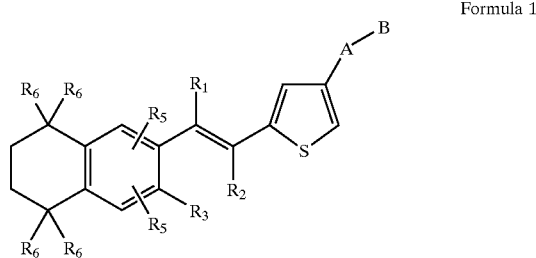

Formula 1

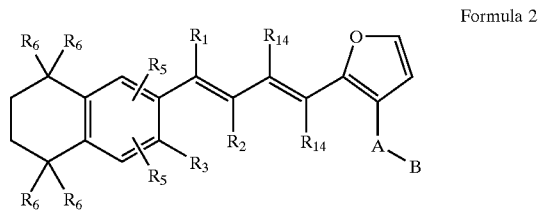

Formula 2

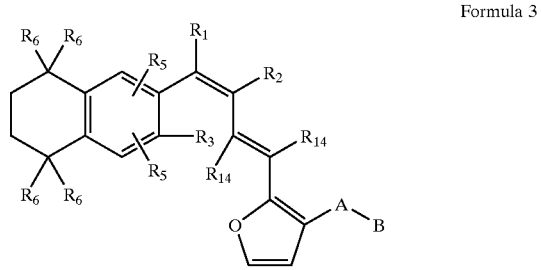

Formula 3

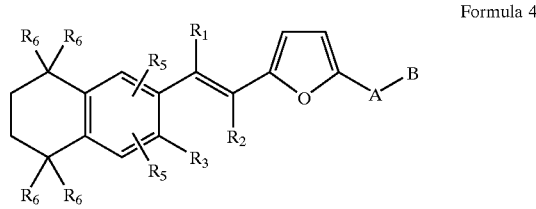

Formula 4

-continued

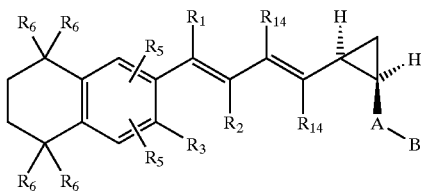

Formula 5

In these general structural formulas the symbols are defined as follows:

$R_1$ is lower alkyl, Cl, Br, or I;

$R_2$ is H, lower alkyl, Cl, Br, or I;

$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;

the $R_5$ groups independently are H, lower alkyl, Cl, Br, I, lower alkoxy or lower thioalkoxy of 1 to 6 carbons;

the $R_6$ groups independently are H or lower alkyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons;

the $R_{14}$ groups independently are H or lower alkyl.

Preferred specific RXR agonist and selective RXR agonist compounds used in the pharamaceuticals compositions and methods of treatment of the present invention are those, where $R_1$ represents lower alkyl, still more preferably methyl.

With reference to the symbol $R_2$ those compounds are preferred for use in the present invention where $R_2$ is H or lower alkyl, more preferably H.

Regarding the group $R_3$, those compounds are preferred where $R_3$ is lower alkyl, more preferably methyl.

Regarding the groups $R_5$, compounds are prefered for use in the present invention where $R_5$ is H or lower alkyl, more preferably H.

Regarding the groups $R_6$, compounds are preferred for use in the present invention where $R_6$ are lower alkyl, more preferably methyl.

With respect to the group —A—B— compounds are preferred for use in the present invention where —A—B— is a $(CH_2)_n$—$COOR_8$ group, or a $(CH_2)_n$—$CONR_9R_{10}$ group ($R_8$, $R_9$ and $R_{10}$ defined as above), and more preferably where n is zero, and where the B group is $COOR_8$.

With respect to the groups $R_{14}$ in the compounds of Formula 2, 3, and 5, compounds are preferred for use in the present invention where $R_{14}$ is hydrogen.

Specific examples of preferred compounds of the present invention are shown by their respective structural formulas below, and are designated Compound 1 (AGN 191701), Compound 2 (AGN 192198), Compound 3 (AGN 191985), Compound 4 (AGN 192171), and Compound 5 (AGN 191758). The structure of the reference compound AGN 191440, (Compound 6) is also shown.

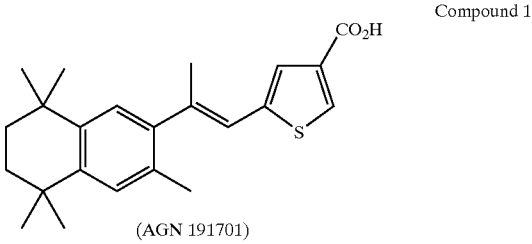

21

Compound 6

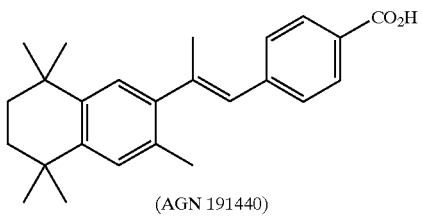

(AGN 191440)

Compound 7

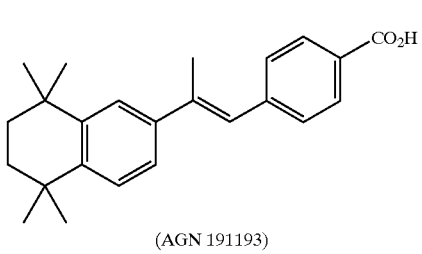

(AGN 191193)

22

Synthetic Procedures for Obtaining the Compounds in Accordance with the Invention The compounds set forth above as general and specific examples of specific and selective RXR agonists which can be used in the pharmaceutical compositions and methods of treatment of the present invention, can be made by a number of different synthetic chemical pathways. To illustrate the invention the following synthetic schemes are provided. The synthetic chemist will readily appreciate that the conditions set out here are specific embodiments which can be generalized within the skill of the practicing synthetic organic chemist.

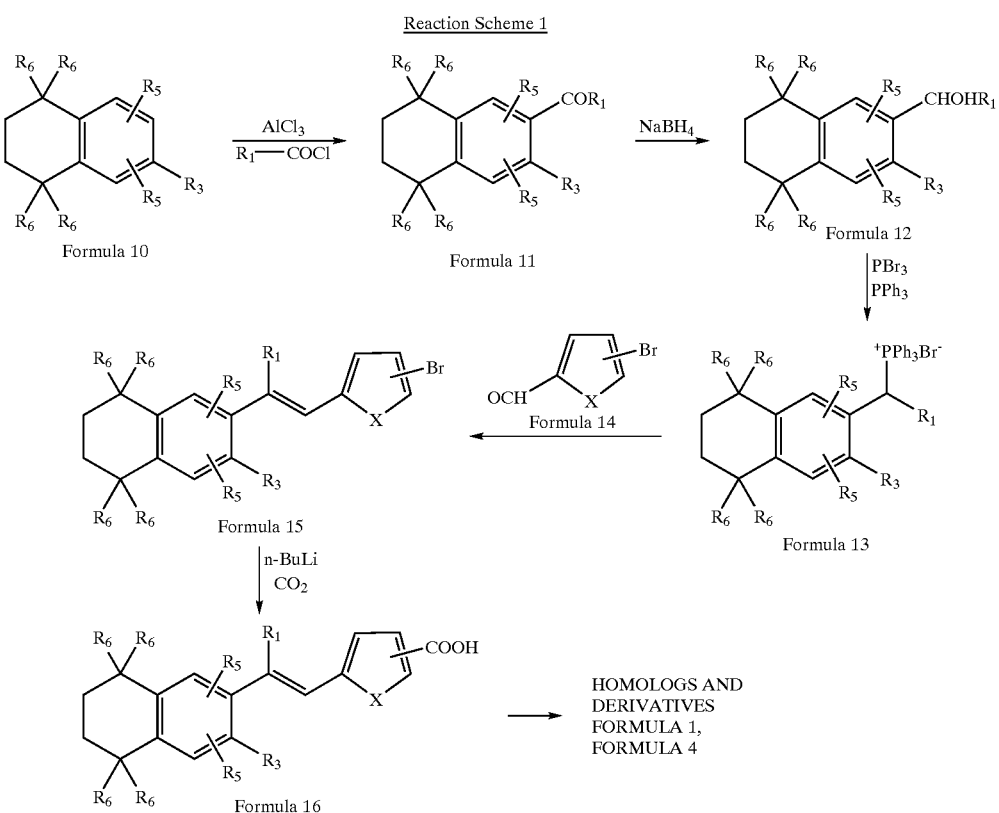

Reaction Scheme 1

Reaction Scheme 1 illustrates a synthetic process for obtaining compounds of Formula 1 and of Formula 4. In accordance with this synthetic scheme, a 5,6,7,8-tetrahydronaphthyl compound of Formula 10 which has the desired $R_3$, $R_5$, and $R_6$ substituents (as these are defined in connection with Formula 1 and Formula 4) is reacted under Friedel Crafts-like conditions with a reagent such as $R_1COCl$ ($R_1$ is defined as in connection with Formula 1 and Formula 4) to introduce the $R_1$—CO-ketone function into the 2-position of the tetrahydronaphthalene nucleus. When $R_1$ is methyl, then the reagent in the Friedel Crafts type reaction is typically acetyl chloride. The resulting ketone of Formula 11 is then reduced (for example with sodium borohydride) to the corresponding alcohol of Formula 12. The alcohol of Formula 12 is converted to the corresponding phosphonium salt (for example triphenyl phosphonium bromide) by treatment with the appropriate reagents, such as phosphorous tribromide and triphenylphosphine. The phosphonium salt of Formula 13 is a Wittig reagent, which is reacted with a bromo thiophene aldehyde or bromo furaldehyde of Formula 14, under Wittig conditions (base such as n-butyl lithium) to provide compounds of Formula 15. The bromo group of the heterocyclic moiety of the compound of Formula is converted into a carboxyl group by reaction with n-butyl lithium and capture of carbon dioxide, to yield the carboxylic acid compounds of Formula 16, which can be further converted into further homologs and derivatives, as described herein. The synthetic sequence of Reaction Scheme 1 is particularly suited for preparation of the thiophene compounds of Formula 1, and is the preferred synthetic route for the preparation of Compound 1 (AGN 191701) in accordance with the invention.

An alternative synthetic route leading to compounds of Formula 1 and of Formula 4 is described with reference to Reaction Scheme 2.

Reaction Scheme 2

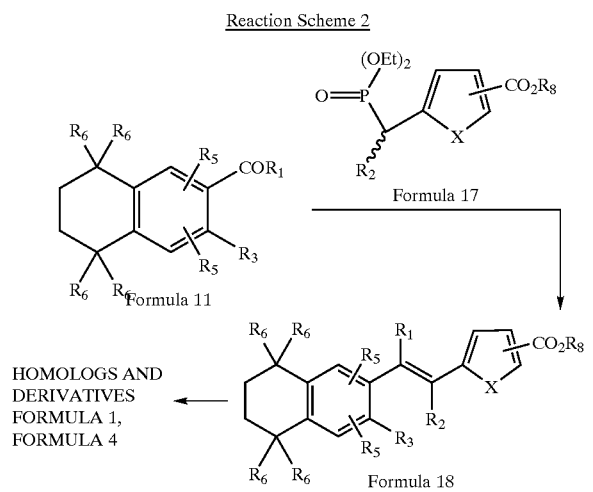

Formula 17

Formula 18

HOMOLOGS AND DERIVATIVES FORMULA 1, FORMULA 4

In accordance with Reaction Scheme 2, the ketone compound of Formula 11 is subjected to a Wittig Horner type reaction with a phosphonate reagent of Formula 17. The phosphonate reagent of Formula 17 carries an ester ($COOR_8$) substituent, but it should be understood that an analogous phosphonate reagent can, generally speaking, carry the A—B functionality, as such functionality is defined in connection with Formula 1 and Formula 4. The Wittig Horner type reaction is typically conducted in the presence of strong base, such as $NaCH_2SOCH_3$ (dimsyl sodium) in a solvent like tetrahydrofuran (THF). The synthetic procedure of Reaction Scheme 2 is the preferred route for obtaining compounds of Formula 4, and is preferred for the preparation of Compound 4 (AGN 192171). The procedure of Reaction Scheme 2 (with appropriate modification of reagents) is also the preferred synthetic route to making AGN 191440 (Compound 6), which is the reference compound used in the RXR receptor activity assay.

The compounds of Formula 16 and of Formula 18 may be subjected to further transformations, particularly as far as synthetic transformation of the $COOR_8$ group is concerned. As far as the preparation of compounds analogous to the compounds of Formula 16 and of Formula 18, but differing therefrom in the functionality of the A—B group is concerned, (and by extension of the principles to any and all compounds used in accordance with the invention) the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before affecting the Wittig reaction, the Wittig Horner reaction, or analogous coupling reactions of Reaction Scheme 1 and Reaction Scheme 2 (where the necessary reagents corresponding to Formula 14 and/or to Formula 17 are not available from a commercial source) the carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

An alternative means for making compounds where A is $(CH_2)_n$ (n is 1–5) is to subject the compounds of Formula 1–5 where B is an acid or other function, to homologation, using the Arndt-Eistert method referred to above, or other homologation procedures.

Compounds of Formula 1–5, where A is an alkenyl group having one or more double bonds can be made for example, by having the requisite number of double bonds incorporated into the intermediate which is coupled as a phosphonate with the ketone of Formula 11. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-arylalkyl-carboxylic acid, ester or like carbox-aldehyde. Compounds of Formula 1–5 where the A group has a triple (acetylenic) bond can be made by using the corresponding phosphonate intermediate. Such intermediate can be obtained by reactions well known in the art, for example, by reaction of a corresponding aromatic-methyl ketone with strong base, such as lithium diisopropyl amide.

The acids and salts derived from compounds of Formula 1–5 are readily obtainable from the corresponding esters. Basic saponification with an alkali metal base will provide the acid. For example, an ester may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron, 1978. 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Referring back again to Reaction Schemes 1 and Reaction Schemes 2, those skilled in the art will readily recognize that further variations of the therein described Wittig and Wittig Horner reactions are possible to obtain compounds which are within the scope of the present invention. For example, the Wittig reaction shown in Reaction Scheme 1 can be performed with reagents where a tetrahydronaphtalene derivative analogous to Formula 13 bears a keto group, and where a heteroaromatic compound analogous to Formula 14 bears the triphenylphosphonium moiety. The Wittig Horner reaction of Reaction Scheme 2 can be performed with reagents where a tetrahydronaphtalene derivative analogous to Formula 11 bears a dialkylphosphonate moiety and where a heteroaromatic compound analogous to Formula 17 bears a keto or aldehyde function.

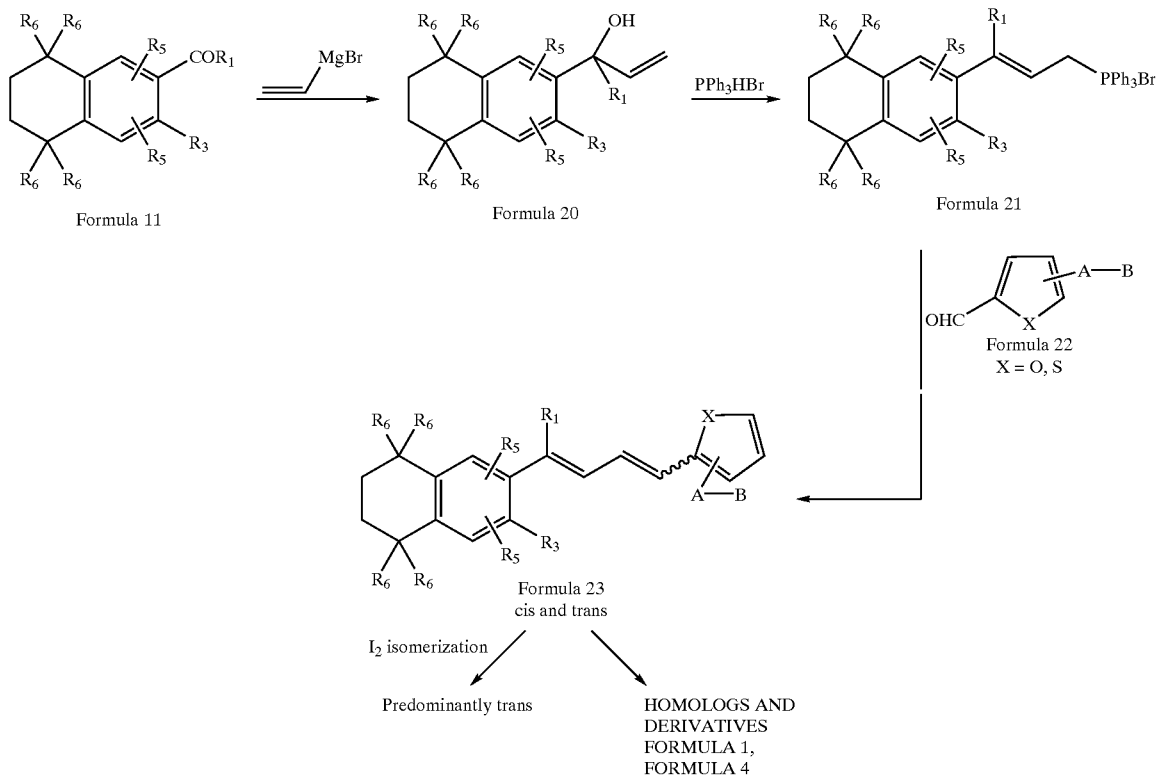

Reaction scheme 3

Referring now to Reaction Scheme 3, a general route for the preparation of compounds of Formula 2 and of Formula 3 is disclosed. The ketone of Formula 11 is reacted with vinyl magnesium bromide to give the tertiary alcohol of Formula 20. The alcohol of Formula 20 is reacted with triphenylphosphine hydrobromide. This reaction results in migration of the double bond and formation of the triphenylphosphonium salt of Formula 21 where the triphenylphosphonium moiety is attached to a primary carbon. The double bond obtained in this process is usually predominantly of trans (E) configuration. The triphenylphosphonium salt of Formula 21 is a Wittig reagent, which is reacted with the heteroaryl aldehyde of Formula 22, where X is S or O, to provide the conjugated diene compounds of Formula 23. The double bond formed in the last-mentioned Wittig reaction is usually a mixture of cis (Z) and trans (E) isomers. The latter double bond is however isomerized by treatment with iodine in toluene to provide predominantly the trans (E) isomer. In any event, the cis (Z) and trans (E) isomers can be separated by appropriate techniques, such as high pressure liquid chromatography (HPLC). The compounds of Formula 23 can be converted into further homologs and derivatives, such as compounds of Formula 2 and 3, as described above in connection with Reaction Schemes 1 and 2.

The above-summarized synthetic route of Reaction Scheme 3 is the preferred method for making compounds of Formula 2 and of Formula 3 in accordance with the present invention where X is O, and is the preferred method for making Compound 2 (AGN 192198) and Compound 3 (AGN 191985).

and 3, as described above. The synthetic route of Reaction Scheme 4 is the preferred method for making Compound 5 (AGN 191758).

Specific Examples

Methyl [3,5,5,8,8-Pentamethyl(5,6,7,8-tetrahydronaphthalen)-2-yl] Ketone (Compound 10)

To a suspension of 6.71 g (50.3 mmol) of aluminum chloride in methylene chloride at 0° C. under argon was added a solution of 3.95 g (3.58 mL, 50.3 mmol) of acetyl chloride and 10.21 g (41.9 mmol) of 3,5,5,8,8-pentamethyl-5,6,7,8-tetrahydronaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, anddried ($MgSO_4$). Solvent was removed in-vacuo and the resulting residue purified using flash chromatography to give the title compound as an ivory solid.

PMR ($CDCl_3$): δ 1.28 (6H, s), 1.30 (6H, s), 1.69 (4H, s), 2.49 (3H, s), 2.57 (3H, s), 7.15 (1H, s), 7.67 (1H, s).

(±)-1-(5,6,7,8-Tetrahydro-3,5,5,8,8-pentamethylnaphthalen-2-yl)ethanol (Compound 11)

To a solution of 4.17 g (17.1 mmol) of methyl [3,5,5,8,8-pentamethyl(5,6,7,8-tetrahydronaphthalen-2-yl] ketone

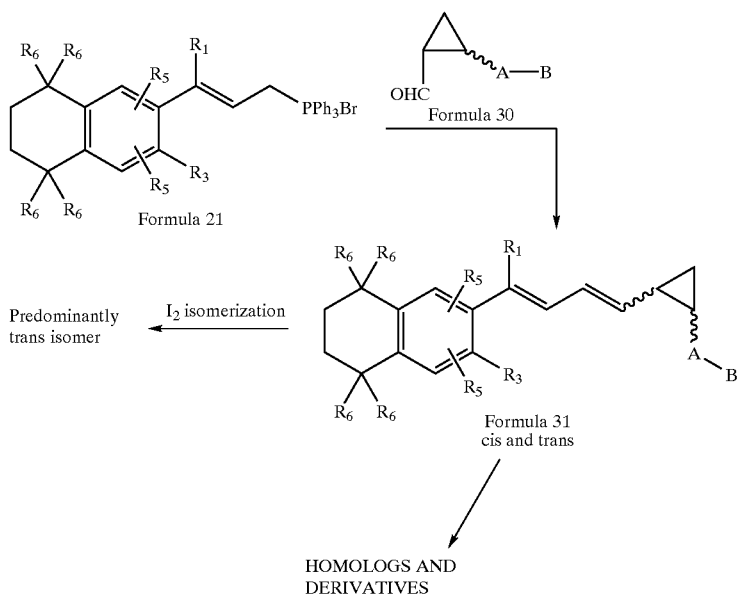

Reaction Scheme 4

Reaction Scheme 4 illustrates a synthetic route to compounds of Formula 5. The triphenylphosphonium salt of Formula 21 is reacted with the cyclopropane aldehyde derivative of Formula 30 to provide the diene compound of Formula 31. The double bond formed in the last mentioned reaction is a mixture of cis (Z) and trans (E) isomers, but the ratio of the trans (E) isomer can be increased by isomerization with iodine. The cis and trans isomers, in this case also, can usually be separated by appropriate techniques such as high pressure liquid chromatography (HPLC). The compounds of Formula 31 can be converted into further homologs and derivatives, such as compounds of Formula 2

(Compound 10) in methanol at 0° C. was portionwise added 0.77 g (20.4 mmol) of sodium borohydride and the resulting suspension stirred at 0° C. for 4 hours. Solvent was removed in-vacuo and the resulting solid taken-up in water, acidified using 1N HCl, and extracted three times with ether. The ether extracts were washed with water, brine and dried ($MgSO_4$). The solvent was removed in-vacuo and resulting residue purified using flash chromatography ($SiO_2$, 10% ethyl acetate in hexanes) to give a single isomer: the title compound as a white solid.

PMR (CDCl$_3$): δ 1.28 (12H, m), 1.47 (3H, d, J=6.5 Hz), 1.67 (4H, s), 2.49 (3H, s), 5.08 (1H, m), 7.10 (1H, s), 7.45 (1H, s).

[(5,6,7,8-Tetrahydro-3,5,5,8,8-pentamethylnaphthalen-2-yl)ethan-1-yl] triphenylphosphonium Bromide (Compound 12)

To a solution of 3.87 g (15.7 mmol) of (±)-1-(5,6,7,8-tetrahydro-3,5,5,8,8-pentamethylnaphthalen-2-yl)ethanol (Compound 11) in ether and hexanes at 0° C. under argon, was added 42.4 g (14.9 mL, 157 mmol) of phosphorus tribromide and the resulting mixture stirred for 2 hours. Water was then dropwise added over a period of 30 minutes and the layers separated. The aqueous layer was extracted three times with ether. The ether layers were washed with water, brine, and dried (MgSO$_4$). The solvent was removed in-vacuo and the remaining residue taken-up in benzene. Triphenylphosphine was added and the mixture stirred at room temperature for 24 hours. The mixture was then concentrated in-vacuo and the resulting solid recrystallized from acetonitrile and ethyl acetate and hexanes to give the title compound as a white solid.

PMR (CDCl$_3$): δ 0.61 (3H, s), 0.89 (3H, s), 1.27 (6H, s), 1.62 (4H, m), 1.85 (6H, d), 2.04 (3H, dd), 5.19 (2H, m), 6.62 (1H, d), 7.02 (1H, s), 7.43 (6H, m), 7.68 (6H, m), 7.87 (3H, m).

2-[(E)-2-(5,6,7,8-Tetrahydro-3,5,5,8,8-pentamethyl-2-naphthalen-2-yl)proren-1-yl]-4-bromothiophene (Compound 13)

To a solution of 0.56 g (0.98 mmol) of 1-(3,5,5,8,8-pentamethyl-5,6,7,8-tetrahydro-naphthalen-2-yl)ethan-1-yltriphenylphosphonium bromide (Compound 12) in 11 mL of tetrahydrofuran at −78° C. under argon was added dropwise 0.41 g (0.61 mL, 0.98 mmol, 1.6 M in hexanes) of n-BuLi. The resulting suspension was allowed to warm to room temperature and then a solution of 0.28 g (1.47 mmol) of 4-bromo-2-thiophenecarboxaldehyde in 2 mL of tetrahydrofuran was dropwise added and the resulting mixture stirred for 20 hours at room temperature. The solvent was removed in-vacuo and the resulting solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 0.5% ethyl acetate in hexanes) to give the title compound as a white solid.

PMR (CDCl$_3$): δ 1.27 (6H, s), 1.29 (6H, s), 1.68 (4H, s), 2.26 (6H, m), 6.45 (1H, s), 6.75 (1H, s), 6.95 (1H, s), 7.07 (1H, s), 7.11 (1H, s), 7.17 (1H, s).

2-[(E)-2-(5,6,7,8-Tetrahydro-3,5,5,8,8-pentamethylnaphthalen-2-yl)propen-1-yl]thiophene-4-carboxylic Acid (Compound 1)

To a solution of 500 mg (1.24 mmol) of 2[-2-(E)-(5,6,7,8-tetrahydro-3,5,5,8,8-pentamethylnaphthalen-2-yl)propen-1-yl]-4-bromothiophene (Compound 13) in 15 mL of tetrahydrofuran stirring under argon at −100° C. was added 0.527 g (0.775 mL, 1.24 mmol, 1.6 M in hexanes) of n-BuLi. The reaction was stirred for two minutes and purged with carbon dioxide for 20 minutes. The reaction mixture was then allowed to warm to room temperature, acidified, and extracted using ether. The ether extracts were washed with water, brine and dried (MgSO$_4$). The solvent was removed in-vacuo and the resulting residue taken-up in aqueous 2N sodium hydroxide and washed with ether. The resulting aqueous layer was acidified using 1N HCl and extracted with ether. The ether layer was washed with water and brine, and dried (MgSO$_4$). The solvent was removed in-vacuo and the resulting material purified by flash chromatography (10% ethyl acetate in hexanes) to give the title compound as a white solid.

PMR (d$^6$-DMSO): δ 1.23 (12H, s), 1.62 (4H, s), 2.21 (3H, s), 2.23 (3H, s), 6.56 (1H, s), 7.07 (1H, s), 7.13 (1H, s), 7.45 (2H, s), 8.24 (2H, s).

Ethyl 2-(5-Bromomethyl)furancarboxylate (Compound 20)

To a suspension of 1.32 g (7.4 mmol) of N-bromosuccinimide and 10.9 mg of benzoyl peroxide in 8 mL of carbontetrachloride was added a solution of ethyl-2-(5-methyl)furancarboxylate in 8 mL of carbon-tetrachloride and the resulting mixture stirred at 55° C. for 8 hours. The mixture was then filtered, concentrated and residual oil purified using flash chromatography (SiO$_2$, 5% ethyl acetate in hexanes) to give the title compound as a clear oil.

PMR (CDCl$_3$): δ 1.38 (3H, t, J=7.1 Hz), 4.37 (2H, q, J=7.1 Hz), 6.51 (1H, d, J=3.5 Hz), 7.15 (1H, d, J=3.4 Hz).

Ethyl 2-[5-(Diethoxyphosphinyl)methyl] furancarboxylate (Compound 21)

A solution of 1.84 g (1.30 ml, 14.8 mmol) of triethylphosphite and 0.84 g (3.6 mmol) of ethyl-2-(5-bromomethyl)furancarboxylate (Compound 20) was heated at 125° C. under argon for 30 hours. The solution was then cooled and purified using kuegelrohr distillation (165–180° C., 1 mm Hg) to give the title compound as a clear oil.

PMR (CDCl$_3$): δ 1.36 (9H, m), 3.30 (2H, d, J=21.4 Hz), 4.12 (4H, p, J=7.1 Hz), 4.34 (2H, q, J=7.2 Hz), 6.41 (1H, t, J=3.2 Hz), 7.13 (1H, d, J=3.4 Hz).

Ethyl 5-[(E)-2-(5,6,7,8-Tetrahydro-3,5,5,8,8-pentamethylnaphthalen-2-yl)propen-1-yl]-2-furancarboxylate (Compound 22)

A mixture of sodiumhydride in 10 mL of dimethylsulfoxide was heated at 55° C. for 1 hour and added to 1.159 g (4.00 mmol) of ethyl-2-[5-(diethoxyphosphinyl)methyl] furanoate (Compound 21). The resulting deep red solution was stirred 45 minutes at room temperature and added to a solution of 0.501 g (2.05 mmol) of methyl (3,5,5,8,8-pentamethyl(5,6,7,8-tetrahydronaphthalen)-2-yl] ketone (Compound 10) and the resulting solution stirred at room temperature for 48 hours. Sodium bicarbonate was added and the solution extracted using ether and dried (MgSO$_4$). The solution was concentrated and the residual oil purified using column chromatography (SiO$_{2,5}$% ethyl acetate in hexanes). Separation of isomers was achieved using HPLC.

PMR (CDCl$_3$): δ 1.27 (6H, s), 1.29 (6H, s), 1.39 (3H, t, J=7.1 Hz), 1.68 (4H, s), 2.27 (3H, s), 2.35 (3H, s), 4.37 (2H, q, J=7.1 Hz), 6.31 (1H, s), 6.43 (1H, d, J=3.6 Hz), 7.07 (1H, s), 7.10 (1H, s), 7.22 (1H, d, J=3.6 Hz).

5-[(E)-2-(5,6,7,8-Tetrahydro-3,5,5,8,8-pentamethylnaphthalen-2-yl)propen-1-yl)] Furan 2-Carboxylic Acid (Compound 4)

To a solution of 61 mg of lithium hydroxide-monohydrate (1.4 mmol) in 0.5 ml of water, 1.0 ml of ethanol, and 1.5 ml of methanol was added 49 mg (0.13 mmol) of ethyl 5-[2-(E)-((5,6,7,8-tetrahydro-3,5,5,8,8-pentamethylnaphthalen)-2-yl)propen-1-yl]-2-furancarboxylate (Compound 22) and the resulting mixture stirred at room temperature for 48 hours. Solvent was removed in-vacuo and the resulting solid taken-up in water, acidified using 2N HCl, and extracted with ether. The ether extracts were washed with water, brine and dried ($MgSO_4$). The solvent was removed in-vacuo to give the title compound as a white solid.

PMR ($CDCl_3$): δ 1.28 (6H, s), 1.29 (6H, s), 1.68 (4H, s), 2.28 (3H, s), 2.37 (3H, s), 6.33 (1H, s), 6.48 (1H, d, J=3.4 Hz), 7.08 (1H, s), 7.11 (1H, s), 7.38 (1H, d, J=3.4 Hz).

2-[3,5,5,8,8,-Pentamethyl-5,6,7,8-tetrahydronapthalen)-2-yl]-but-3-en-2-ol (Compound 30)

To a stirred solution of 5.36 g (21.9 mmol) of methyl [3,5,5,8,8,-pentamethyl (5,6,7,8-tetrahydronapthalen)-2-yl] ketone (Compound 10) dissolved in 38 ml of freshly distilled tetrahydrofuran at 0 C under argon was added 37.4 ml of 1.0M solution of vinyl magnesium bromide in tetrahydrofuran dropwise via syringe. The resulting mixture was allowed to warm to room temperature over a period of 2 hours with stirring. The mixture was recooled to 0 C and saturated aqueous ammonium chloride solution was added dropwise. The mixture was then extracted with ether and the ether layers were washed with water, saturated sodium bicarbonate, brine, and dried (MgSO4). The solvent was removed in-vacuo and the residue purified using flash chromatography (SiO2, 3% ethyl acetate in hexanes) to give the title compound as a white solid.

PMR (CDCl3): d 1.26 (6H, s), 1.27 (6H, s), 1.66 (4H, s), 1.70 (3H, s), 2.40 (3H, s), 5.14 (1H, dd, J11 Hz, J1.2 Hz), 5.23 (1H, dd, J17 Hz, J1.2 Hz), 6.16 (1H, dd, J11 Hz, J17 Hz), 7.04 (1H, s), 7.40 (1H, s).

Triphenyl [3-(5,6,7,8-Tetrahydro-3,5,5,8,8,-pentamethyl-2-naphthalenyl)-2-buten-yl] Phosphonium Bromide (E) (Compound 31)

To a solution of 6.30 g (18.4 mmol) triphenylphosphonium bromide in 50 ml of methanol was added 5.02 g (18.4 mmol) of 2-[3,5,5,8,8,-pentamethyl-5,6,7,8-tetrahydronapthalen)-2-yl]-but-3-en-2-ol (Compound 30) in 50 ml of methanol via addition funnel dropwise at room temperature under argon. The solvent was removed in-vacuo after 16 hours of stirring and the residue was purified using flash chormatography (SiO2, 5% methanol in methylene chloride) to give the title compound as a white foam.

PMR(CDCl3): 1.21 (6H, s), 1.23 (6H, s), 1.63 (4H, s), 1.80 (3H, d, J6 Hz), 2.06 (3H, m), 4.84 (2H, m), 5.31 (1H, s), 6.78 (1H, s), 7.0 (1H, s), 7.65–7.97 (15H, m).

Methyl [2-[4-Methyl-4-(3,5,5,8,8,-pentamethyl-5,6,7,8-tetrahydronapthalen)-2-yl]-1E,3E-butadien-1-yl] 3-Furanoate (Compound 32) and Methyl [2-[4-Methyl-4-(3,5,5,8,8,-pentamethyl-5,6,7,8-tetrahydronapthalen)-2-yl]-1Z,3E-butadien-1-yl] 3-Furanoate (Compound 33)

A suspension of triphenyl [3-(5,6,7,8-tetrahydro-3,5,5,8,8,-pentamethyl-2-naphthalenyl)-2-buten-yl] phosphonium bromide (E) (1.5 g, 2.51 mmol Compound 31), 3-carbomethoxy-2-furaldehyde (387 mg, 2.51 mmol, M. Valenta, Collect. Czech. Chem. Commun. 1969, (6) 1814–18) and 1,2-epoxybutane (7 ml) were combined under argon and warmed to reflux for 24 hours. The resulting solution was concentrated in vacuo, and the residue was purified using flash chromatography ($SiO_2$, 10% ethyl acetate in hexanes) to give a mixture of geometrical isomers. To increase the yield of the trans isomer about the disubstituted double bond, a solution of the isomeric mixture in 30 ml toluene and 40 ml ether was treated with 30 mg (0.01 mmol) of iodine, and stirred under argon for 24 hours. The solvent was removed by evaporation and the residue was purified by flash chromatography ($SiO_2$, 10% ethyl acetate in hexanes). The geometrical isomers were separated by reverse HPLC (Partisil ODS-2; 11% $H_2O$ in acetonitrile) to give the title compounds as clear pale yellow oils.

PMR ($CDCl_3$) for the 1E, 3E (trans, trans) title compound: d 1.26 (12H, s), 1.67 (4H, s), 2.20 (3H, d, J=1.0 Hz.), 2.26 (3H, s), 3.84 (3H, s), 6.20 (1H, dd, J=11.5 1 Hz.), 6.72 (1H, d, J=1.9 Hz), 7.06 (1H, s), 7.07 (1H, d, J=15.6 Hz.), 7.10 (1H, s), 7.30 (1H, d, J=1.9 Hz.) 7.35 (1H, dd, J=11.5, 15.6 Hz.)

PMR ($CDCl_3$) for the 1Z, 3E (cis, trans) title compound: d 1.25 (3H, s), 1.30 (3H, s), 1.69 (4H, s), 2.12 (3H, s), 2.16 (3H, s), 3.83 (3H, s), 6.34 (1H, d, J=11 Hz.), 6.64 (1H, d, J=2 Hz.), 6.65 (1H, dd, J=11, 16 Hz), 6.97 (1H, s), 7.00 (1H, d, J=16 Hz), 7.11 (1H, s), 7.16 (1H, d, 2 Hz).

2-[4-Methyl-4-(3,5,5,8,8,-pentamethyl-5,6,7,8-tetrahydronapthalen)-2-yl]-1Z,3E-butadien-1-yl] Furan 3-Carboxylic Acid (Compound 3)

266 mg (0.69 mmol) of methyl [2-[4-methyl-4-(3,5,5,8,8,-pentamethyl-5,6,7,8-tetrahydronapthalen)-2-yl]-1Z,3E-butadien-1-yl] 3-furanoate (Compound 33) was suspended in 5.5 ml of tetrahydrofuran and 2.75 ml of 0.5M LiOH solution (1.4 mmol, 33.6 mg). The suspension was warmed to reflux for 18 hours. The solution was evaporated to dryness. The residue was dissolved in 250 ml $H_2O$ and washed with 100 ml of ethyl ether. The aqueous phase was layered with 100 ml of ethyl ether and brought to pH=1 with 12M HCl. The aqueous layer was washed with ethyl ether (3×100 ml). The organic fractions were pooled, washed with brine, dried over MgSO4, and evaporated to give the title compound as a white solid.

PMR (d6-DMSO); δ 1.23 (12H, s), 1.62 (4H, s), 2.15 (3H, s), 2.20 (3H, s), 6.08 (1H, dd, J=10.4, 1.3 Hz), 7.03 (1H, s), 7.11 (1H, s), 7,18 (1H, dd, J=16.6, 10.4 Hz), 7.31 (1H, d, J=16.6 Hz), 7.32–7.36 (1H, m), 7.51–7.57 (1H, m), 7.77 (1H, dd, J=7.8, 1.2 Hz), 7.88 (1H, d, J=7.9 Hz).

2-[4-Methyl-4-(3,5,5,8,8,-pentamethyl-5,6,7,8-tetrahydronapthalen)-2-yl]-1E,3E-butadien-1-yl] Furan 3-Carboxylic Acid (Compound 2)

Using the same procedures as the above example, starting with 480 mg (1.27 mmol) of methyl [2-[4-meth-yl-4-(3,5,5,8,8,-pentamethyl-5,6,7,8-tetrahydronapthalen)-2-yl]-1E,3E-butadien-1-yl] 3-furanoate (Compound 32), 10 ml of tetrahydrofuran and 5.0 ml of 0.5M LiOH (2.50 mmol, 60 mg), gave the title compound as a white solid.

PMR (CDCl3); δ 1.28 (6H, s), 1.29 (6H, s), 1.68 (4H, s), 2.21 (3H, s), 2.25 (3H, s), 6.20 (1H, d, J=12.0 Hz), 6.77 (1H, d, J=1.9 Hz), 7.05 (1H, s), 7.08 (1H, d, J=15.0 Hz), 7.09 (1H, s), 7.33 (1H, d, J=1.9 Hz), 7.38 (1H, dd, J=15.0, 12.0 Hz).

Ethyl cis-[2-[4-Methyl-4-(3,5,5,8,8,-pentamethyl-5,6,7,8-tetrahydronapthalen)-2-yl]-1E,3E-butadien-1-yl] 1-Cyclopronane Carboxylate (Compound 40

A suspension of of triphenyl [3-(5,6,7,8-tetrahydro-3,5,5,8,8,-pentamethyl-2-naphthalenyl)-2-buten-yl] phosphonium bromide (E) (1.0 g, 1.7 mmol, Compound 31) dissolved in 2 ml of tetrahydrofuran, ethyl 2-formyl-1-cyclopropane carboxylate (0.242 g 0.225 ml, 1.7 mmol, available from Aldrich Chemical Co.) and 1,2-epoxybutane (5.86 g, 7 ml, 81.3 mmol) were combined under argon and heated at 65 C for 72 hours. The mixture was cooled to room temperature and solvent was removed in-vacuo. The residue was purified using flash chromatography (SiO2, 3% ethyl acetate in hexanes) to give a mixture of isomers. To the mixture of isomers in 10 ml of dry ether was added 30 mg (0.01 mmol) of iodine at room temperature, exposed to light, stirring for 40 hours, in order to increase the yield of the trans isomer about the double bond attached to the cyclopopane ring. Thereafter, the isomers were sepearated using HPLC (1% ethyl acetate in hexanes) to give the title compound as a clear oil.

PMR (CDCl3): 0.87–0.95 (1H, m), 1.20–1.38 (16H, m), 1.54–1.62 (1H, m), 1.68 (4H, s), 1.86–1.94 (1H, m), 2.00 (3H, s), 2.14 (3H, s), 4.09 (2H, q), 5.10 (1H, dd, J=15.3 Hz, J=9.2 Hz), 5.85 (1H, dd, J=15.3 Hz, J=11.0 Hz), 6.03 (1H, d, J=11.0 Hz), 6.92 (1H, s), 7.09 (1H, s).

Cis-[2-[4-Methyl-4-(3,5,5,8,8,-pentamethyl-5,6,7,8-tetrahydronapthalen)-2-yl]-1E,3E-butadien-1-yl] 1-Cyclopropane Carboxylic Acid (Compound 5

A solution of ethyl cis-[2-[4-methyl-4-(3,5,5,8,8,-pentamethyl-5,6,7,8-tetrahydronapthalen)-2-yl]-1E,3E-butadien-1-yl] 1-cyclopropane carboxylate (0.024 g, 0.0632 mmol, Compound 40) in 1 ml of methanol and 5.6 mg (0.05 ml, 0.10 mmol) of 2N potassium hydroxide/methanol solution was stirred at reflux under argon for 48 hours. An additional 5.6 mg (0.05 ml, 0.10 mmol) of 2N potassium hydroxide/methanol solution was added to the mixture and refluxed for 10 hours. The mixture was cooled to room temperature and solvent removed in-vacuo. The resulting mixture was then taken up in water and the aqueous layer was acidified using 80:20 ETOAC/HCl to PH=4, and extracted with ether. The ether extracts were washed with water, brine and dried (MgSO4). The solvent was removed in-vacuo to give the title compound as a colorless oil.

PMR (CDCl3): 0.94–1.00 (1H, m), 1.22–1.33 (13H, m), 1.58–1.62 (1H, m), 1.70 (4H, s), 1.75–1.85 (1H, m), 1.99 (3H, s), 2.14 (3H, s), 5.25 (1H, dd, J=15.1 Hz, J=9.3 Hz), 5.84 (1H, dd, J=15.1 Hz, J=10.8 Hz), 6.10 (1H, d, J=10.8 Hz), 6.98 (1H, s), 7.19 (1H, s).

4-Carboethoxy-benzylbromide (Compound 50)

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzylbromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 hours. The mixture was allowed to cool to room temperature and the resultant white precipitate removed by filtration. The filtrate was washed with water, dried (MgSO$_4$) and then concentrated in-vacuo to give the title compound as a colorless oil which crystallized on standing. PMR (CDCl$_3$); δ 1.39 (3H, t, J=7.2 Hz), 4.38 (2H, q, J=7.2 Hz), 4.50 (2H, s), 7.45 (2H, d, J=7.7 Hz), 8.03 (2H, d, J=7.7 Hz).

Ethyl [4-(Diethoxyphosphinyl)methyl]benzoate (Compound 51)

A mixture of 11.8 g (48 mmol) of 4-carboethoxybenzylbromide (Compound 50) and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120=° C. for 3 hours at which time no further ethyl bromide was being formed. The residue was purified by vacuum distillation to give the title compound as a colorless oil, BP=170°/0.35 mm). PMR (CDCl$_3$): δ 1.23 (6H, t, J=7.1 Hz), 1.39 (3H, t, J=6.9 Hz), 3.21 (2H, d, J=22.1 Hz), 4.02 (4H, m), 4.37 (2H, q, J=7.5 Hz), 7.38 (2H, d, J=7.9 Hz), 8.00 (2H, d, J=7.9 Hz).

Ethyl 4-[(E)-2-(5,6,7,8-Tetrahydro-3,5,5,8,8-pentamethylnaphthalen-2-yl)propen-1-yl]benzoate (Compound 52)

A solution of 5.0 g (21.5 mmol) of methyl [3,5,5,8,8-pentamethyl(5,6,7,8-tetrahydro-naphthalen)-2-yl] ketone (Compound 10) and 3.39 g (11.3 mmol) of ethyl [4-(diethoxyphosphinyl)methyl]benzoate, (Compound 51) in 25 mL of tetrahydrofuran was added via cannula into a suspension of 0.52 g (21.5 mmol) of sodium hydride in 25 mL of tetrahydrofuran at 0° C. under argon. The resulting suspension was allowed to warm to room temperature and stirred for 16 hours. The resulting sludge was taken-up in water and 1N HCl and extracted with ether. The ether layers were washed with water, brine, and dried (MgSO$_4$). The solvent was removed in-vacuo and the residue purified using flash chromatography (SiO$_2$, 1% ethyl acetate in hexanes) to give a mixture of isomers which were separated using HPLC (0.5% ethyl acetate in hexanes) to give the title compound as a white solid.

PMR (CDCl$_3$): δ 1.30 (12H, s), 1.38 (3H, t, J=7.0 Hz), 1.69 (4H, s), 2.21 (3H, s), 2.30 (3H, s), 4.39 (2H, q, J=7.1 Hz), 6.42 (1H, s), 7.12 (2H, overl. s), 7.43 (2H, d, J=8.3 Hz), 8.05 (2H, d, J=8.3 Hz).

4-(E)-2-(5,6,7,8-Tetrahydro-3,5,5,8,8-pentamethylnabhthalen-2-yl)propen-1-yl]benzoic Acid (Compound 6)

A solution of potassium hydroxide in ethanol was added to 95 mg (0.25 mmol) of ethyl 4-[(E)-2-(5,6,7,8-tetrahydro-3,5,5,8,8-pentamethylnapth)-2-yl)propen-1-yl]benzoate (Compound 52) and the resulting mixture stirred at room temperature. Solvent was removed in-vacuo and the resulting solid taken-up in water, acidified using 1N HCl, and extracted three times with ether. The ether extracts were washed with water, brine and dried (MgSO$_4$). The solvent was removed in-vacuo to give the title compound as an orange solid.

PMR (d$^6$-DMSO): δ 1.23 (12H, s), 1.62 (4H, s), 2.15 (3H, s), 2.23 (3H, s), 6.37 (1H, s), 7.08 (1H, s), 7.13 (1H, s), 7.51 (2H, d, J=8.3 Hz), 7.94 (2H, d, J=8.3 Hz).

What is claimed is:

1. A process for treating or preventing in a host mammal, one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound wherein the active compound has retinoid like activity and is a selective agonist of RXR retinoid receptor sites in preference over RAR retinoid receptor sites.

2. The process of claim 1 wherein the active compound binds at least approximately ten times stronger to RXR retinoid receptor sites than to RAR retinoid receptor sites.

3. The process of claim 2 wherein approximately 0.01 to 100 ml/kg body weight of the active compound is administered systemically to the female mammal per day.

4. The process of claim 3 wherein approximately 0.1 to 10 mg/kg body weight of the active compound is administered systemically to the female mammal per day.

5. A process for treating or preventing in a female mammal, who is in child bearing age or pregnant one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound wherein the active compound has retinoid like activity and is a selective agonist of RXR retinoid receptor sites in preference over RAR retinoid receptor sites.

6. The process of claim 2 wherein the active compound is administered topically in a pharmaceutical composition where the active compound is present in a concentration approximately between 0.001 to 5.0 per cent by weight.

7. The process of claim 6 wherein the active compound is administered topically in a pharmaceutical composition where the active compound is present in a concentration approximately between 0.01 to 1.0 per cent by weight.

8. A process for treating or preventing in a host mammal, one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound wherein the active compound has retinoid-like biological activity and the further biological property that the compound is a selective agonist of RXR retinoid receptor sites in preference over RAR retionoid receptor sites, and wherein in an assay conducted to measure the agonist-like binding activity of the active compound to RAR and RXR receptor sites, in which assay binding to RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl)propen-1-yl]benzoic acid, the $EC_{50}$ concentration of the active compound in the RXR receptor sites is at least 10 times less than the $EC_{50}$ of the active compound in RAR receptor sites.

9. The process of claim 8 wherein approximately 0.01 to 100 mg/kg body weight of the active compound is administered systemically to the female mammal per day.

10. The process of claim 9 wherein approximately 0.1 to 10 mg/kg body weight of the active compound is administered systemically to the female mammal per day.

11. A process for treating or preventing in a female mammal, who is in child bearing age or pregnant one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound wherein the active compound has retinoid-like biological activity and the further biological property that the compound is a selective agonist of RXR retinoid receptor sites in preference over RAR retinoid receptor sites, and wherein in an assay conducted to measure the agonist-like binding activity of the active compound to RAR and RXR receptor sites, in which assay binding to RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl)propen-1-yl]benzoic acid, the $EC_{50}$ concentration of the active compound in the RXR receptor sites is at least 10 times less than the $EC_{50}$ of the active compound in RAR receptor sites.

12. The process of claim 11 wherein the active compound is administered topically in a pharmaceutical composition where the active compound is present in a concentration approximately between 0.001 to 5.0 per cent by weight.

13. The process of claim 12 wherein the active compound is administered topically in a pharmaceutical composition where the active compound is present in a concentration approximately between 0.01 to 1.0 per cent by weight.

14. A process for treating or preventing in a host mammal, one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound wherein the active compound has retinoid-like biological activity and the further biological property that the compound is a selective agonist of RXR retinoid receptor sites in preference over $RAR_\alpha$, $RAR_\beta$, and $RAR_\gamma$ retinoid receptor sites, said selectivity being measured in an assay in which binding to the $RAR_\alpha$, $RAR_\beta$, and $RAR_\gamma$ receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl)propen-1-yl]benzoic acid, and wherein the respective $RAR_\alpha$, $RAR_\beta$, $RAR_\gamma$ and RXR receptors are expressed in Hela cells which have been transfected with plasmids coding for the respective $RAR_\alpha$, $RAR_\beta$, $RAR_\gamma$ and RXR receptors, and in which assay the $EC_{50}$ concentration of the active compound in the RXR receptor sites is measured to be at least 10 times less than the $EC_{50}$ of the active compound in the RAR receptor sites.

15. The process of claim 14 wherein approximately 0.01 to 100 mg/kg body weight of the active compound is administered systemically to the female mammal per day.

16. The process of claim 15 wherein approximately 0.1 to 10 mg/kg body weight of the active compound is administered systemically to the host mammal per day.

17. A process for treating or preventing in a female mammal, who is in child bearing age or pregnant one or more of the diseases and conditions selected from the group consisting of dermatoses, malignant hyperproliferative diseases, atherosclerosis and restenosis resulting from neointimal hyperproliferation, non-malignant hyperproliferative diseases autoimmune diseases, immunological disorders, chronic inflammatory diseases, diseases associated with lipid metabolism and transport dry eye syndrome, for promoting wound healing, and for reversing and preventing the effects of sun damage to skin by administering a pharmaceutical composition containing an effective dose of an active compound, wherein the active compound has retinoid-like biological activity and the further biological property that the compound is a selective agonist of RXR retinoid receptor sites in preference over $RAR_\alpha$, $RAR_\beta$, and RAR retinoid receptor sites, said selectivity being measured in an assay in which binding to the $RAR_\alpha$, $RAR_\beta$, and RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl)propen-1-yl]benzoic acid, and wherein the respective $RAR_\alpha$, $RAR_\beta$, RAR and RXR receptors are expressed in Hela cells which have been transfected with plasmids coding for the respective $RAR_\alpha$, $RAR_\beta$, RAR and RXR receptors, and in which assay the $EC_{50}$ concentration of the active compound in the RXR receptor sites is measured to be at least 10 times less than the $EC_{50}$ of the active compound in the RAR receptor sites.

18. The process of claim 14 wherein the active compound is administered topically in a pharmaceutical composition where the active compound is present in a concentration approximately between 0.001 to 5.0 per cent by weight.

19. The process of claim 18 wherein the active compound is administered topically in a pharmaceutical composition where the active compound is present in a concentration approximately between 0.01 to 1.0 per cent by weight.

20. A compound characterized by its biological property that the compound is a selective agonist of RXR retinoid receptor sites in preference over RAR retionoid receptor sites, and wherein in an assay conducted to measure the agonist-like binding activity of the active compound to RAR and RXR receptor sites, in which assay binding to RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl)propen-1-yl]benzoic acid, the $EC_{50}$ concentration of the active compound in the RXR receptor sites is at least 10 times less than the $EC_{50}$ of the active compound in RAR receptor sites.

21. A process for activating an RXR retinoid receptor in preference over RAR retinoid receptor in a mammal by administering to said mammal in need of such activation a pharmaceutical composition containing an effective dose of an active compound wherein the active compound has retinoid-like biological activity and the further biological property that the compound is a selective agonist of RXR retinoid receptor sites in preference over $RAR_\alpha$, $RAR_\beta$, and $RAR_\Gamma$ retinoid receptor sites.

22. The process of claim 21 wherein the active compound binds at least approximately ten times stronger to RXR retinoid receptor sites than to RAR retinoid receptor sites.

23. The process of claim 22 wherein approximately 0.01 to 100 mg/kg body weight of the active compound is administered systemically to the host mammal per day.

24. The process of claim 23 wherein the pharmaceutical composition is administered to a female mammal who is in child bearing age or pregnant.

25. The process of claim 22 wherein the active compound is administered topically in a pharmaceutical composition where the active compound is present in a concentration approximately between 0.001 to 5.0 per cent by weight.

26. The process of claim 21 wherein in an assay conducted to measure the agonist-like binding activity of the active compoundto RAR and RXR receptor sites, in which assay binding to RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl) propen-1-yl]benzoic acid, the $EC_{50}$ concentration of the active compound in the RXR receptor sites is at least 10 times less than the $EC_{50}$ of the active compound in RAR receptor sites.

27. The process of claim 21 wherein the selectivity of the active compound for RXR receptor sites over RAR receptor sites is measured in an assay in which binding to the $RAR_\alpha$, $RAR_\beta$, and RAR receptor sites of the test compound is compared to trans retinoic acid, and the binding to RXR receptor sites of the test compound is compared to 4-(E)-2-(5,6,7,8-tetrahydro-3,5,5,8,8-pentamethylnaphthalen-2-yl) propen-1-yl]benzoic acid, and wherein the respective $RAR_\alpha$, $RAR_\beta$, $RAR_\Gamma$ and RXR receptors are expressed in Hela cells which have been transfected with plasmids coding for the respective $RAR_\alpha$, $RAR_\beta$, $RAR_\Gamma$ and RXR receptors, and in which assay the $EC_{50}$ concentration of the active compound in the RXR receptor sites is measured to be at least 10 times less than the $EC_{50}$ of the active compound in the RAR receptor sites.

* * * * *

UNITED STATES PATENT AND TRADEMARK OFFICE
CERTIFICATE OF CORRECTION

PATENT NO.    : 6,627,652 B1
DATED         : September 30, 2003
INVENTOR(S)   : Chandraratna et al.

It is certified that error appears in the above-identified patent and that said Letters Patent is hereby corrected as shown below:

Column 2,
Line 50, "6i" should be -- 6 --

Column 8,
Line 45, "Density Gradients" should be -- density gradients --

Column 10,
Lines 41-42, "weight(g)/ACETONE x 1/mol. Wt.(g/mol) x 100ml/.005mol/L = ml/L" should be
-- $\frac{weight}{ACETONE \text{ mol. wt. (g/mol)}} \times \frac{1}{.005 mol/L} \times \frac{100ml}{L} = ml$ --

Column 15,
Line 16, "≦" should be -- ≤ --

Column 23,
Line 15, "Formula" should be -- Formula 15 --

Column 28,
Line 6, "Pentamethyl" should be -- pentamethyl --
Line 7, "Ketone" should be -- ketone --
Line 18, "anddried" should be -- and dried --

Column 29,
Line 7, "Bromide" should be -- beomide --
Line 55, "Acid" should be -- acid --

Column 30,
Line 11, "Bromomethyl" should be -- bromomethyl --
Line 24, "Diethoxyphosphinyl" should be -- diethoxyphosphinyl --
Line 37, "Tetrahydro" should be -- tetrahydro --
Line 61, "Carboxylic Acid" should be -- carboxylic acid --

Column 31,
Line 34, "Tetrahydro" should be -- tetrahydro --
Line 36, "Phosphonium Bromide" should be -- phosphonium bromide --
Lines 50 and 53, "Methyl" should be -- methyl --
Lines 52 and 55, "Furanoate" should be -- furanoate --

UNITED STATES PATENT AND TRADEMARK OFFICE
CERTIFICATE OF CORRECTION

PATENT NO. : 6,627,652 B1
DATED : September 30, 2003
INVENTOR(S) : Chandraratna et al.

It is certified that error appears in the above-identified patent and that said Letters Patent is hereby corrected as shown below:

Column 32,
Lines 23 and 46, "Furan" should be -- furan --
Lines 23 and 46, "Carboxylic Acid" should be -- carboxylic acid --
Line 58, "Methyl" should be -- methyl --
Line 60, "Cyclopronane Carboxylate" should be -- cyclopropane carboxylate --

Column 33,
Line 19, "Methyl" should be -- methyl --
Line 21, "Cyclopropane Carboxylic Acid" should be -- cyclopropane carboxylic acid --
Line 61, "Diethoxyphosphinyl" should be -- diethoxyphosphinyl --

Column 34,
Line 9, "Tetrahydro" should be -- tetrahydro --
Line 34, "Acid" should be -- acid --

Column 37,
Line 11, "$_{RAR\beta}$" should be -- $RAR_\beta$ --
Line 25, "The process of claim 14" should be -- The process of claim 17 --

Column 38,
Line 23, "compoundto" should be -- compound to --

Signed and Sealed this

Ninth Day of November, 2004

JON W. DUDAS
*Director of the United States Patent and Trademark Office*